(12) United States Patent
Abbott et al.

(10) Patent No.: US 6,600,076 B1
(45) Date of Patent: Jul. 29, 2003

(54) CLEAVABLE, WATER-SOLUBLE SURFACTANTS

(75) Inventors: Nicholas L. Abbott, Madison, WI (US); Lana I. Jong, Hillsboro, OR (US)

(73) Assignees: The Regents of the University of California, Oakland, CA (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/416,094

(22) Filed: Oct. 12, 1999

Related U.S. Application Data

(63) Continuation-in-part of application No. 09/286,497, filed on Apr. 5, 1999, now abandoned.

(51) Int. Cl.[7] .............................................. C07C 321/00
(52) U.S. Cl. .......................... 568/21; 568/22; 516/198
(58) Field of Search ...................... 568/21, 22; 516/198

(56) References Cited

U.S. PATENT DOCUMENTS 3,640,715 A * 2/1972 Hückstadt et al.

FOREIGN PATENT DOCUMENTS

WO      WO 93/06832      4/1993

OTHER PUBLICATIONS

Barltrop, et al., "The Chemistry of 1,2–dithiolane (trimethylene disulfide) as a model for the primary quantum conversion act in photosynthesis," *J. Am. Chem Soc.*, 76:4348–4367 (1954).
Cuomo, et al., "Synthesis and properties of unsymmetrical aryl glucosyl disulfides: models for a new class of cleavable nonionic detergents," *J. Org. chem.*, 45:4216–4219 (1980).
Gallardo, et al., "Active control of interfacial properties: A comparison of dimeric and monomeric ferrocenyl surfactants at the surface of aqueous solutions," *Langmuir*, 13203:208 (1997).

Gravina, et al., "Thioltransferase is a specific glutathionyl mixed disulfide oxidoreductase," *Biochemistry*, 32:3368–3376 (1993).
Holmberg, "Surfactants with controlled half–lives," *Curr. Opin. Colloid Interface Sci..* 1:572–579 (1996).
Jaeger, "Cleavable surfactants," *Supramolecular chemistry*, 5:27–30 (1995).
Lamoureux, et al., "Synthesis of dithiols as reducing agents for disulfides in neutral aqueous solution and comparison of reduction potentials," *J. Org. Chem.*, 58:633–641 (1993).
Pinazo, A., et al., "Synthesis and properties of cationic surfactants containing a disulfide bond," *J. Am. Oil Chem. Soc.*, 70:37–42 (1993).
Ringsdorf, et al., "Molecular architecture and function of polymeric oriented systems: Models for the study of organization, surface recognition, and dynamics of biomembers," *Angew, Chem., Int. Ed. Engl.*, 27(1):113–158 (1998).
Samuel, et al., "Polymerized–depolymerized vesicles. Reversible thiol–disulfide–based phosphatidylcholine membranes," *J. Am. Chem. Soc.*, 107:42–47 (1988).
Zagal, et al., "Electrochemistry of cysteine and cystine on metal–phthalocyanines adsorbed on a graphite electrode," *Electrochim. Acta*, 30:449–454 (1985).
Taylor, K., et al., "Studies on substrate specificity of hog liver flaving–containig monoxygenase. Anionic organic sulfur compounds," *Biochem. Pharmacol.*, 36(1):141–6 (1987); *Chem. Abstr.*, vol. 106, Abstract No. 98481, (1987) (Columbus, OH).
Jong, L., et al., "Rate–dependent lowering of surface tension during transformation of water–soluble surfactants from bolaform to monomeric structures," *Langmuir*, 14(9):2235–2237 (1998), *Chem. Abstr.*, vol. 129, Abstract No. 86361, (1998) (Columbus, OH).

* cited by examiner

*Primary Examiner*—Paul J. Killos
(74) *Attorney, Agent, or Firm*—Townsend and Townsend and Crew LLP

(57) ABSTRACT

The present invention provides a novel class of water-soluble cleavable surfactants and methods for utilizing these surfactants.

29 Claims, 22 Drawing Sheets

1

5

6

0 MIN (A)

10 MIN (B)

45 MIN (C)

24 HR (D)

ACID-CATALYZED HYDROLYSIS

| Chemodegradable Surfactant | Ref | Conditions | Time | Surface Tension/ CMCs | Stability | Synthesis | Reaction Products |
|---|---|---|---|---|---|---|---|
| DIOXOLANE | 11 | 5.5 M HCl 25°C | 200 min | CMC = 16 μM in 0.01 M NaHCO$_3$ $\gamma_{init}$ = 32 mN/m $\gamma_{fin}$ = 49 mN/m | — | See ref. | $(C_4H_9)_2C=O$ $(CH_2)_8N^+(CH_3)_3$ $CH_3SO_3^-$ |
| DIOXOLANE (BETAINE) | 12 | 2% DCl 25°C | 48 hr | CMC = 0.95 mM $\gamma_{lim}$ = 30 mN/m $\gamma_{init}$ = 30 mN/m $\gamma_{fin}$ = 51 mN/m | — | See ref. | |
| DIOXANE | 13 | 0.1 M DCl 27°C | 13 hr | CMC = 60.2 mM $\gamma_{lim}$ = 29.3 mN/m 31°C | — | See ref. | $C_7H_{15}CH=O$ $(CH_2OH)_2CHOSO_3Na$ |
| QUATERNARY HYDRAZINIUM | 14 | a. i. NaNO$_2$, 2.2 M HCl, 0°C ii. 10% NaOH b. Na$_2$S$_2$O$_4$, 1.7 M NaOH, 95°C | a. 16 hr b. 12 hr | CMC = 7.1 mM $\gamma_{lim}$ = 35 mN/m | — | See ref. | $C_{12}H_{25}N(CH_3)_2$ |

FIG. 20A.

| | | | | |
|---|---|---|---|---|
| Gluconolactone<br>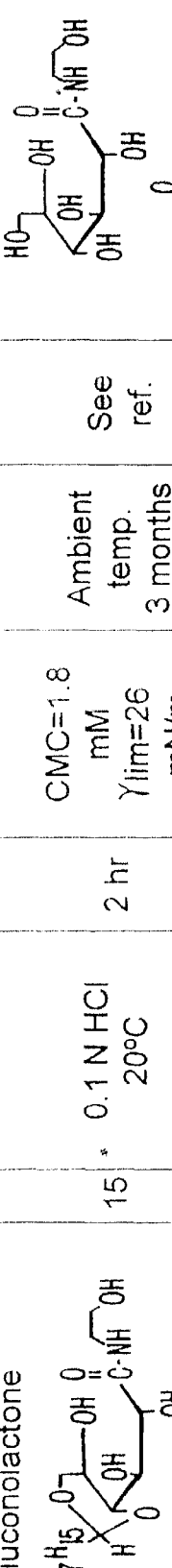 | 15 | 0.1 N HCl<br>20°C | 2 hr | CMC=1.8 mM<br>γlim=26 mN/m | Ambient temp.<br>3 months | See ref. | 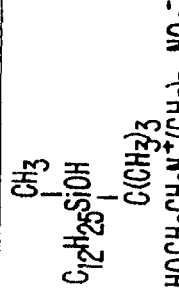 |
| Silicon-oxygen<br>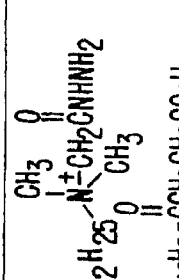 | 8 | 3.3 M DCl<br>20°C | 2 hr | CMC=28 uM in 0.01 M NaHCO$_3$ | Stable in pH 3-12, but hydrolyzes outside range, cleaved by F- | See ref. | 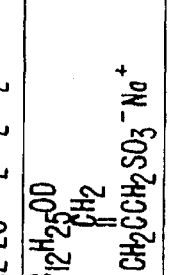 |
| Carbon-nitrogen<br> | 16 | 0.1 M CD$_3$CO$_2$D<br>25°C | 24 hr | -- | | one-step | 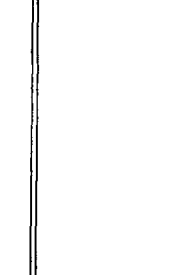 |
| Epichlorohydrin<br>CH$_2$<br>C$_{12}$H$_{25}$OCH$_2$OCH$_2$SO$_3^-$ Na$^+$ | 17 | DCl, pD3<br>25°C | 30 min | CMC=1 mM<br>γlim=34.5 mN/m | -- | See ref. |  |
| Poly(ethylene glycol) monomethyl ether (MPEGOH)<br>MPEGO $-$CH$_2$CH(CH$_3$)CH$_2$C(CH$_3$)$_3$<br>MW=550 | 18 | 5% H$_2$SO$_4$, pH 3<br>25°C | 1.5 hr | CMC=0.3 mM<br>γlim=25.1 mN/m | Stable in 5% NaOH, 24 hr. | See ref. | -- |

FIG. 20B.

| BASE-CATALYZED HYDROLYSIS | | | | | |
|---|---|---|---|---|---|
| β-aryloxy sulfone  C₁₂H₂₅–C₆H₄–SO₂–CH₂–CH₂–O–C₆H₄–N⁺(CH₃)₃ NO₃⁻ | 19 | 0.1 M NaHCO₃ 25°C | 10 min | CMC=76 uM in 0.01 M CH₃CO₂H | Stable in acid, 24 hr, up to 75°C | See ref. | C₁₂H₂₅–C₆H₄–SO₂CH=CH₂   HO–C₆H₄–N⁺(CH₃)₃ NO₃⁻ |
| Acetyldecyl trimethylammonium iodide | 20 | 0.1 M NaOD, pH 13 25°C | <5 min | CMC= 25 mM | Stable in 0.01 M DCl, 140 hr. | ketone structure   N(CH₃)₃ |
| Ester quats  O=C(OCH₂C(CH₃)₃N⁺(CH₃)₃Br⁻)(CH₂)₁₃CH₃ | 21 | 50 mM phosphate buffer, pH 7.9 | 2 hr | — | — | two-step | CH₃(CH₂)₁₃OH   Br⁻ N⁺(CH₃)₃CH₂CO₂⁻ |

CLEAVABLE, WATER-SOLUBLE SURFACTANTS

CROSS REFERENCE TO RELATED APPLICATIONS

This application claims priority to, and is a Continuation-in-Part, of U.S. Ser. No. 09/286,497, filed on Apr. 5, 1999 abandoned and entitled "Cleavable, Water-Soluble Surfactants," the disclosure of which is incorporated herein by reference in its entirety for all purposes.

GOVERNMENT RIGHTS

This invention was made with United States Government support awarded by the following agency: NSF 9896374. The work disclosed herein was also partially supported by a grant from National Science Foundation (CTS-9410147 and CTS-9502263). The United States Government may have certain rights in this invention.

BACKGROUND OF THE INVENTION

Surfactants are well known materials that can be generally described as having a hydrophobic moiety and a hydrophilic group per molecule. A wide variety of these materials are known and they have numerous uses such as emulsifiers, detergents, dispersants and solubilizing agents in the fields of cosmetics, textile treatment, industrial and personal cleaning preparations, corrosion inhibitors and the like.

Surfactants can be anionic, cationic, amphoteric or nonionic. Anionic surfactants carry a negative charge on the hydrophilic portion, usually in the form of a carboxylate, phosphate, sulfate or sulfonate. These surfactants find use in emulsion polymerization as well as in agricultural chemicals, personal care and household products, industrial and institutional cleaners. They function as emulsifiers, cleaners, wetting agents, foaming and frothing agents for shampoos, car washes, carpet shampoos, hand dishwashing, latex foaming, oil recovery and other industrial uses. See, generally *Kirk-Othmer Encyclopedia of Chemical Technology*, 4$^{th}$ Edition, John Wiley and Sons, New York, 1997, Vol. 23, pp. 478–541.

Cationic surfactants carry a positive charge on the hydrophilic moiety, most generally in the form of an amine or quaternary ammonium salt. These surfactants are used, for example, as textile softeners, conditioning agents, dispersants, emulsifiers, wetting agents, sanitizers, dye-fixing agents, foam stabilizers and corrosion inhibitors. See, for example, Drew et al., U.S. Pat. No. 3,001,945, issued Sep. 26, 1961.

Nonionic surfactants carry no charge when they are dissolved in an aqueous medium. The hydrophilicity in these surfactants is the result of hydrogen bonding interactions between the surfactant and the aqueous medium. Nonionic surfactants are generally derivatives of polyoxyethylenes.

Surfactants are frequently employed in the treatment of wastewater and waste products from various sources to stabilize emulsions. Surfactant stabilized emulsions can lead to sludge generation, high costs for disposal, recovery of recyclable materials, and other problems. Emulsions of waste products can create significant environmental problems because they are usually extremely difficult to convert into more valuable, useful or innocuous products. Further, they are usually not readily susceptible to emulsion breaking techniques and separation into aqueous and organic phases. As the incineration of the organic waste component of an emulsion requires the removal of substantial amounts of water, the inability to separate the emulsion into aqueous and burnable fractions further complicates production and recycling efforts.

Efforts have been directed to producing compounds having surfactant properties that can be "turned off" as a result of a structural change in the surfactant, producing a class of surfactants that are "chemodegradable" (See, Jaeger, *Supramolecular Chemistry* 5: 27–30 (1995); Holmberg, *Curr. Opin. Colloid Interface Sci.* 1: 572–579 (1996)). "Chernodegradable surfactants" are surface-active compounds that can undergo specific chemical reactions and thereby lose their surface activity (Sokolowksi et al., *J. Am. Oil Chem. Soc.* 69: 633–638 (1992)).

Chemodegradable surfactants have attracted substantial interest in the recent past for several reasons (Holmberg, supra). For example, the capability to transform water-soluble molecules from surface-active states to surface-inactive ones, can be used to break emulsions or foams following their use in lubricant formulations (White, *Chemical Processing* 60: 32–32 (1997)). Chemodegradable surfactants are also useful as emulsifiers in emulsion polymerizations because their subsequent conversion to surface inactive-states can be exploited to eliminate the presence of charged surfactant head groups at surfaces of latex particles, increasing the water resistance of resultant polymer films. (Mezger, et al., *Progress in Organic Coatings* 29, 147–157 (1996)) Chemodegradable surfactants are also potentially useful in procedures such as those used for the isolation, purification and reconstitution of proteins in lipid environments. The surfactants can be used to solubilize membrane proteins, but can then be transformed into fragments that are readily displaced by natural phospholipids (Cuomo et al., *J. Org. Chem.* 45:4216–4219 (1980).

Although the known chemodegradable surfactants exhibit interesting properties, they are not ideal for a number of reasons. In general, these agents are hampered by their slow degradation upon contact with the cleavage reagent, and the need to use great excesses of the cleavage reagent to achieve quantitative cleavage. Other agents are rendered of comparatively little use due to their low water solubility, instability in solutions that are acidic or basic, and the need to be stored and used under restrictive conditions.

Chemodegradable surfactants comprising a disulfide moiety have been investigated. The disulfide-containing degradable surfactants are generally poorly water-soluble. Although two water-soluble, disulfide-containing, cationic surfactants have been reported, these compounds are rapidly degraded in aqueous solutions having a pH greater than 8. Furthermore, these agents are not described as being degradable by either oxidation or reduction, rather these agents are described as interacting with, and binding to, kerastin fibers through a disulfide exchange reaction. Moreover, these agents are not used to reversibly form or to disrupt emulsions (Pinazo, A. et al., *J. Am. Oil Chem. Soc.* 70:37–42 (1993)).

An ideal chemodegradable surfactant should meet a number of criteria. First, the incorporation of a chemodegradable group in the surfactant should not unduly complicate the synthesis of the surfactant. Also, the surface properties of chemodegradable surfactants should not be compromised relative to classical surfactants prior to their transformation into less surface-active species. Furthermore, the chemodegradable surfactants must be water-soluble and stable under a range of conditions (e.g., broad pH range, light, heat, etc.). Moreover, the transformation of the chemodegradable surfactant into its less surface-active state should be effected without requiring a large excess of a transforming agent.

Presently available chemodegradable surfactants do not meet each of these criteria, however, quite surprisingly, the present invention provides surfactants meeting these criteria and methods of using these surfactants.

SUMMARY OF THE INVENTION

It has now been discovered that surfactants containing a disulfide bond within their framework, which can be cleaved or made more hydrophilic by an oxidant, meet the criteria set forth above. The present surfactants are substantially water-soluble and thus, are useful for reversibly stabilizing water-based emulsions. The reversible emulsions can be disrupted following the cleavage or increase in hydrophilicity of the disulfide bond via an oxidative process.

The compounds of the invention possess a number of advantages over known chemodegradable surfactants. For example, the present surfactants are quickly cleaved by inexpensive, readily-available and mild oxidants, such as sodium hypochlorite. Often the cleavage is complete in five minutes or less. Moreover, the cleavage process is a one-step process and, unlike prior art acid- and base-cleavable surfactants, the process does not require any subsequent neutralization steps. Furthermore, the molecules of the invention are easily assembled and characterized using art-recognized organic synthetic methods.

Thus, in a first aspect, the present invention provides a substantially water-soluble surfactant according to Formula (I):

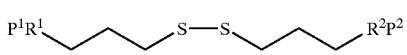

wherein: $P^1$ and $P^2$ are members independently selected from the group consisting of anionic groups, cationic groups, neutral hydrophilic groups and zwitterionic groups; and $R^1$ and $R^2$ are members independently selected from $C_1$ to $C_{24}$ straight-chain alkyl, $C_1$ to $C_{24}$ branched-chain alkyl, $C_1$ to $C_{24}$ straight-chain substituted alkyl and $C_1$ to $C_{24}$ branched-chain substituted alkyl.

In a second aspect, the present invention provides a substantially water-soluble surfactant according to Formula (II):

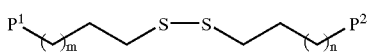

wherein: $P^1$ and $P^2$ are members independently selected from the group consisting of anionic groups, cationic groups, neutral hydrophilic groups and zwitterionic groups; m is a number from 0 to 24, inclusive and n is a number from 0 to 24, inclusive.

In a third aspect, the present invention provides a substantially water-soluble surfactant according to Formula (III):

$$P^1R^1—S—S—R^2P^2 \quad (III)$$

wherein: $P^1$ and $P^2$ are members independently selected from the group consisting of anionic groups, cationic groups, neutral hydrophilic groups and zwitterionic groups; $R^1$ and $R^2$ are members independently selected from $C_1$ to $C_{24}$ straight-chain alkyl, $C_1$ to $C_{24}$ branched-chain alkyl, $C_1$ to $C_{24}$ straight-chain substituted alkyl and $C_1$ to $C_{24}$ branched-chain substituted alkyl; and the surfactant remains at least 80% intact after 24 hours in aqueous solution at pH 8 or greater.

In a fourth aspect, the invention provides an aqueous solution comprising a surfactant according to Formula (I):

wherein:
$P^1$ and $P^2$ are members independently selected from the group consisting of anionic groups, cationic groups, neutral hydrophilic groups and zwitterionic groups; $R^1$ and $R^2$ are members independently selected from $C_1$ to $C_{24}$ straight-chain alkyl, $C_1$ to $C_{24}$ branched-chain alkyl, $C_1$ to $C_{24}$ straight-chain substituted alkyl and $C_1$ to $C_{24}$ branched-chain substituted alkyl; and the solution is switchable between a first state and a second state by oxidation of the disulfide group of the surfactant.

In a fifth aspect, the invention provides a method for increasing surface tension of an aqueous solution of a surfactant comprising a disulfide moiety, the method comprising: contacting the solution with an oxidant, thereby oxidizing the disulfide moiety.

In a sixth aspect, the invention provides a method for disrupting an emulsion comprising: (a) water; (b) a substantially water-insoluble material; and (c) a substantially water-soluble surfactant comprising a disulfide moiety, the method comprising: contacting the emulsion with an oxidant, thereby oxidizing the disulfide moiety.

In a seventh aspect, the invention provides a method for switching a mixture between an emulsified mixture and a non-emulsified mixture. The emulsified mixture comprises: (a) water; (b) a substantially water-insoluble material; and (c) a substantially water-soluble surfactant comprising a disulfide moiety. The non-emulsified mixture comprises: (a) water; (b) a substantially water-insoluble material; and (c) a substantially water-soluble surfactant comprising a thiol moiety. The method comprises; (a) contacting the emulsified mixture with a reducing agent, thereby cleaving the disulfide and forming the non-emulsified mixture; and (b) contacting the non-emulsified mixture with an oxidant, thereby producing a disulfide and forming the emulsified mixture.

In an eighth seventh aspect, the invention provides a method for producing a transient reduction in the surface tension of a solution or emulsion comprising a disulfide-containing surfactant of the invention. The method comprises contacting the surfactant with a reducing agent.

Other features, objects and advantages of the invention and its preferred embodiments will be apparent from the detailed description which follows.

DETAILED DESCRIPTION OF THE INVENTION AND THE PREFERRED EMBODIMENTS

Definitions

Figure 1:
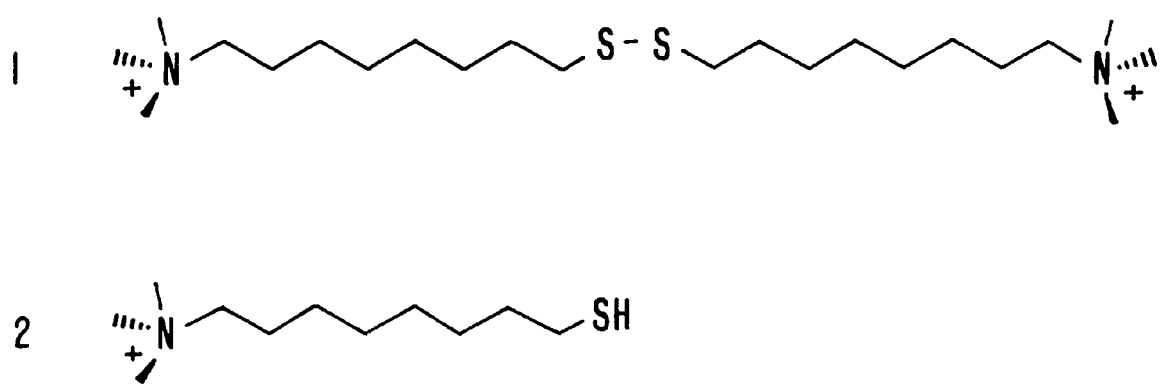
FIG. 1. Chart showing exemplary surfactants of the invention.

"Alkyl" refers to straight- and branched-chain, saturated and unsaturated hydrocarbons. "Lower alkyl", as used herein, refers to "alkyl" groups having from about 1 to about 6 carbon atoms.

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, napthyl, biphenyl, diphenylmethyl and benzophenone among others. The term "aryl" encompasses "arylalkyl."

The term "alkylarene" is used herein to refer to a subset of "aryl" in which the aryl group is substituted with an alkyl group as defined herein.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, wherein R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to describe primary amines, R—$NH_2$, wherein R is alkyl or substituted alkyl, aryl or substituted aryl as defined herein.

The term "alkoxy" is used herein to refer to the —OR group, wherein R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

The term "unsaturated cyclic hydrocarbon" is used to describe a non-aromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Alkylheteroaryl" defines a subset of "heteroaryl" substituted with an alkyl group, as defined herein.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

The term "heterocyclic" is used herein to describe a saturated or unsaturated non-aromatic group having a single ring or multiple condensed rings from about 1 to about 12 carbon atoms and from about 1 to about 4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The term "alkylheterocyclyl" defines a subset of "heterocyclic" substituted with an alkyl group, as defined herein.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

"Substantially water soluble", as used herein, defines a solubility sufficient to allow production of aqueous solutions of surfactant having a concentration of about 0.1 mM or greater, preferably 1 mM, more preferably 2 mM.

"Aqueous", as used herein refers to mixtures (e.g., solutions and emulsions) that comprise water as a component. An "aqueous" mixture can also include organic solvents, which are either miscible or immiscible with water. "Surface tension", as used herein defines the tension at liquid-liquid and liquid-vapor interfaces.

Introduction

The present invention provides substantially water-soluble cleavable disulfide-containing surfactants and methods of using these surfactants. The compounds possess numerous advantages over known cleavable surfactants, and known disulfide-containing surfactants in particular.

The Compounds

In a first aspect, the present invention provides a substantially water-soluble surfactant according to Formula (I):

$$P^1R^1 \diagup\diagdown\diagup S-S \diagdown\diagup\diagdown R^2P^2 \quad (I)$$

wherein: $P^1$ and $P^2$ are members independently selected from the group consisting of anionic groups, cationic groups, neutral hydrophilic groups and zwitterionic groups; and $R^1$ and $R^2$ are members independently selected from $C_1$ to $C_{24}$ straight-chain alkyl, $C_1$ to $C_{24}$ branched-chain alkyl, $C_1$ to $C_{24}$ straight-chain substituted alkyl and $C_1$ to $C_{24}$ branched-chain substituted alkyl.

In a second aspect, the present invention provides a substantially water-soluble surfactant according to Formula (II):

$$P^1 \diagup\diagdown_m \diagup S-S \diagdown\diagup\diagdown_n P^2 \quad (II)$$

wherein: $P^1$ and $P^2$ are members independently selected from the group consisting of anionic groups, cationic groups, neutral hydrophilic groups and zwitterionic groups; m is a number from 0 to 24, inclusive and n is a number from 0 to 24, inclusive.

In a third aspect, the present invention provides a substantially water-soluble surfactant having the structure:

$$P^1R^1-S-S-R^2P^2 \quad (III)$$

wherein: $P^1$ and $P^2$ are members independently selected from the group consisting of anionic groups, cationic groups, neutral hydrophilic groups and zwitterionic groups; $R^1$ and $R^2$ are members independently selected from $C_1$ to $C_{24}$ straight-chain alkyl, $C_1$ to $C_{24}$ branched-chain alkyl, $C_1$ to $C_{24}$ straight-chain substituted alkyl and $C_1$ to $C_{24}$ branched-chain substituted alkyl; and the surfactant remains at least 80% intact after 24 hours in aqueous solution at pH 8 or greater.

In preferred embodiments of these aspects, $P^1$ and $P^2$ are anionic groups. Useful surfactants according to the invention can be formed using substantially any anionic group known in the art, however, in a preferred embodiment, $P^1$ and $P^2$ are anionic groups independently selected from the group consisting of carboxylates, phosphates, sulfonates and sulfites.

Methods of forming compounds comprising these anionic groups are well known in the art. For example, carboxylates are readily formed by the reaction of chloroacetic acid with a nucleophilic group (i.e., amine, hydroxyl, sulfilydryl, etc.) on a component of the nascent surfactant moiety, such as an amine or hydroxyl group. See, for example, *Organic Functional Group Preparations*, Volume III, 2$^{nd}$ Ed., Sandler and Karo, Eds., Academic Press, Inc., San Diego, 1989, pp. 129–156. Sulfates are readily formed by, inter alia, the sulfation of hydroxyl-containing molecules with $SO_3$ or its derivatives and by the reaction of unsaturated compounds with sulfuric acid. See, for example *Organic Functional Group Preparations*, Volume I, 2$^{nd}$ Ed., Sandler and Karo, Eds., Academic Press, Inc., San Diego, 1989, polypeptide. 236–283. Sulfonates are prepared in both industrial and laboratory quantities by numerous methods. See, for example Gilbert et al., *Ind. Eng. Cheem*. 52, 629 (1960); Carson et al., *Ind. Eng. Chem*. 50, 276 (1958). For a review, see, Gilbert *Sulfonation and Related Reactions*, Interscience, New York, 1965. Many other anionic groups and methods of forming them are readily accessible to those of skill in the art.

In another preferred embodiment, the invention provides a surfactant in which $P^1$ and $P^2$ are cationic groups. Substantially any cationic group known in the art is useful in the compounds of the present invention. In a preferred embodiment, the cationic groups are independently selected from the group consisting of quaternary ammonium, protonated amine, protonated amine oxide and phosphonium groups.

In a still further preferred embodiment, the invention provides a compound according to Formula (IV):

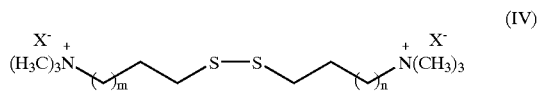

(IV)

wherein, m and n are independently selected from numbers between 0 and 10, inclusive and $X^-$ is a member selected from $Cl^-$, $Br^-$ and $I^-$.

Quaternary ammonium groups are readily prepared by alkylating amine compounds. Protonated amines and amine oxides are well known in the art and are present in acidic solutions. See, Spialter et al, *The Alicyclic Aliphatic Tertiary Amines*, Macmillan, New York, 1965. Moreover, quaternary amine compounds can be easily formed and isolated by incubating a surfactant precursor having a leaving group (e.g., bromo, tosyl, mesyl, etc.) with a tertiary amine. The tertiary amine can bear three identical groups, three different groups or an arrangement of identical and different groups. Upon their replacement of the leaving group, the tertiary amines are quaternized and develop a net positive charge that generally is sufficient to cause the quaternary ammonium adduct to precipitate from solution.

Many nonionic moieties can be used as head group components of the present surfactants including, but not limited to, polyoxyethylene derivatives, carboxylic acid esters, glycerol esters, polyoxyethylene esters, anhydrosorbitol esters, glycol esters of fatty acids, etc,.

In a presently preferred embodiment, $P^1$ and $P^2$ are nonionic groups independently selected from the group consisting of hydroxyl, carboxylic acid esters, alkanolamides, saccharides and poly(ethylene oxide). The preparation of surfactants containing these and other moieties is well known in the art. See, *Kirk-Othmer Encyclopedia of Chemical Technology*, $4^{th}$ Edition, John Wiley and Sons, New York, 1997, Vol. 23, pp. 478–541, ad references therein.

In addition to the groups described above, zwitterionic groups are useful in the compounds of the present invention. In a preferred embodiment, $P^1$ and $P^2$ are zwitterionic groups independently selected from the group consisting of salts of amino acids, salts of amino sulfuric acids and salts of amino sulfurous acids. Methods of forming these compounds are well known in the art.

Alkyl and substituted alkyl groups of many structures are useful components of the present invention. In a preferred embodiment, $R^1$ and $R^2$ are members independently selected from the group consisting of $C_1$ to $C_{24}$ straight-chain alkyl and $C_1$ to $C_{24}$ branched-chain alkyl groups, $C_1$ to $C_{24}$ straight-chain substituted alkyl and $C_1$ to $C_{24}$ substituted branched-chain alkyl groups. In yet another preferred embodiment at least one of $R^1$ and $R^2$ is a fluorocarbon or hydrofluorocarbon.

In each of the compounds of the invention the identity and structure of the polar head groups and the non-polar tail groups can be such that the molecule is either symmetrical or asymmetrical about the disulfide bond. For example, $P^1$ and $P^2$ can be either the same or different. Moreover, the alkyl and/or substituted alkyl groups can be of the same or of different structure.

Water-soluble surfactants containing disulfide bonds are a potentially useful class of amphiphiles because disulfide bonds can be oxidized or reduced chemically (Lamoureux et al., *J. Org. Chem.* 58: 633–641 (1993)), electrochemically (Zagal et al.; *Electrochim. Acta* 30:449–454 (1985)), and photochemically (Barl et al., *J. Am. Chem Soc.* 76:4348–4367 (1954)), can participate in thiol-disulfide exchange reactions, (Samuel et al., *J. Am. Chem. Soc.* 107:42–47 (1988)), and can be processed enzymatically by thiol-disulfide oxidoreductases (Gravina et al., *Biochemistry* 32:3368–376 (1993)). Because previously investigated lipids (Ringsdorf et al., *Angew, Chem., Int. Ed. Engl.* 27:113–158 (1988)) and nonionic amphiphiles (Cuomo et al., *J. Org. Chem.* 45:4216–4219 (1980)), containing disulfide bonds have generally been sparingly soluble in water, these amphiphiles are not useful for studies of surfactancy in aqueous systems.

Compound Synthesis

The compounds of the invention can be synthesized by methods well-known in the art, see, for example Lynn et al., "Surfactants," in *Kirk-Othmer Encyclopedia of Chemical Technology*, Fourth Ed., John Wiley & Sons, New York 1997, 478–541; *Organic Functional Group Preparations*, 2nd Ed., Sandler et al., Eds., Academic Press, Inc., San Diego, 1983; Vogel, *Handbook of Practical Organic Chemistry*, 5th Ed., Furniss et al., Eds., Longman Scientific and Technical/John Wiley & Sons, New York, 1989; *Organic Synthesis Collected Volumes*, John Wiley & Sons, and the references therein, which are incorporated by reference herein. Beginning with these and other art-recognized references, it is well within the capabilities of one of skill in the art to plan and carry out the synthesis of a large array of the disulfide-containing surfactants of the invention using knowledge readily available in the art.

In an exemplary embodiment, compound 1 is prepared by the method set forth in Scheme 1:

Scheme 1

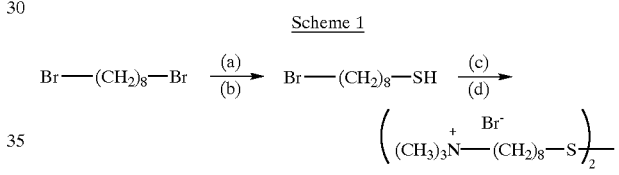

(a) thiolactic acid; (b) HCl/MeOH; (c) $I_2$/EtOH; (d) $(CH_3)_3N$

In Scheme 1, a dihaloalkane is converted to a sulfhydryl by the action of thiolactic acid, followed by hydrolysis of the intermediate thioacetate with dry HCl in MeOH. The disulfide was prepared by the $I_2$ oxidation of a solution of the sulfhydryl. The bromo groups were substituted by incubating a solution of the dibromo-disulfide with excess trimethylamine.

From Scheme 1 it is apparent that characteristics of the dihalo starting material, ("the nucleus") such as its length, degree of saturation and the presence and identity of substituents can be readily varied. Methods of preparing suitable starting materials functionalized with two leaving groups are well-known in the art (see, for example, Vogel *Handbook of Practical Organic Chemistry*, 5th Ed., Furniss et al., Eds., Longman Scientific and Technical/John Wiley & Sons, New York, 1989; *Organic Synthesis Collected Volumes*, John Wiley & Sons, and references therein, each of which is incorporated herein by reference).

Moreover, there are many methods of forming thiols and disulfide linkages that are appropriate for the synthesis of the compounds of the invention. It is well within the abilities of those of skill to choose a method of thiol and/or disulfide formation that is compatible with the functionality present on the nucleus between the leaving groups (see, for example, Chapter 18, "Mercaptans, Sulfides and Disulfides", in *Organic Functional Group Preparations*, 2nd Ed., Sandler et al., Eds., Vol. 1, Academic Press, Inc., San Diego, 1983, and the references therein, which are incorporated herein by reference).

Additionally, there are many straight-forward methods for incorporating the polar head group into the surfactant molecule. One of skill is referred generally to the excellent references cited above for further direction on this aspect of the synthesis of the compounds of the invention.

Surfactant Solutions

In addition to the water-soluble surfactants discussed above, the present invention also provides solutions of these surfactants. These solutions are useful in various applications, including emulsification of wastes or materials for recycling, components of lubricating formulations, emulsification polymerization and the purification and reconstitution of proteins in lipid environments. Other applications for the present compounds and aqueous solutions thereof will be apparent to those of skill in the art (see, generally, Ringsdorf et al., Angewandte Chemie, Int'l Ed. Engl. 27: 113–158 (1988)).

The solutions of the invention can be organic solutions, aqueous solutions or mixtures of organic and aqueous components. It is, however, generally preferred that the solution be an aqueous solution.

Thus, in a seventh aspect, the invention provides an aqueous solution comprising a surfactant according to Formula (I), preferably Formula (II), more preferably Formula (III) and still more preferably Formula (IV). This solution is switchable between a first state and a second state by oxidation of the disulfide group of the surfactant.

The surfactant in the solution can be found entirely in either the first or the second state. Alternatively, it can be present as a mixture of these states (i.e., cleaved surfactant and intact surfactant). The equilibrium concentration of the species in solution can be controlled by the amount of cleavage reagent introduced into the solution.

In a presently preferred embodiment, the solution is a component of an emulsion and oxidizing at least one disulfide group of the surfactant alters an emulsion characteristic which is a member selected from the group consisting of interfacial tension, interfacial elasticity, interfacial viscosity and combinations thereof.

The Methods

The present invention also provides methods for using the compounds of the invention. The compounds of the invention can be used for a wide range of methods, including those set forth in the discussion of the solutions of the compounds of the invention.

Thus, in a further aspect, the invention provides a method for decreasing surface tension of an aqueous solution of a surfactant comprising a disulfide moiety. The method comprises contacting the solution with an oxidant, thereby oxidizing the disulfide moiety.

In further preferred embodiments, the surfactant has a structure according to Formula (I), preferably according to Formula (II), more preferably Formula (III), and more preferably still, Formula (IV).

In a further aspect, the present invention provides a method of disrupting an emulsion comprising: (a) water; (b) a substantially water-insoluble material; and (c) a substantially water-soluble surfactant comprising a disulfide moiety. The method comprises contacting the emulsion with an oxidant, thereby oxidizing the disulfide moiety.

In further preferred embodiments, the surfactant has a structure according to Formula (I), preferably according to Formula (II), more preferably Formula (III), and more preferably still, Formula (IV).

The discussion above concerning the nature of the groups P, P$^2$, R and R$^2$ are generally applicable to this aspect of the invention as well.

The water-soluble surfactant and substantially water-insoluble material can be present in the mixture in any ratio of concentrations. In a preferred embodiment, no more of the surfactant is present than is necessary to stabilize the emulsion.

The substantially water-insoluble material can be any material that is either sparingly miscible or immiscible with water. Examples include oils, fats, waxes and organic solvents (hydrocarbons, ethers, esters, etc.).

In a further aspect, the invention provides a method of switching a mixture between an emulsified mixture and a non-emulsified mixture. The emulsified mixture includes, (a) water; (b) a substantially water-insoluble material; and (c) a substantially water-soluble surfactant comprising a disulfide moiety. The non-emulsified mixture includes, (a) water; (b) a substantially water-insoluble material; and (c) a substantially water-soluble surfactant comprising a thiol moiety. The method comprises (a) contacting the emulsified mixture with a reducing agent, thereby cleaving the disulfide and forming the non-emulsified mixture; and (b) contacting the non-emulsified mixture with an oxidant, thereby producing a disulfide and forming the emulsified mixture. The process is illustrated in Scheme 2.

Scheme 2

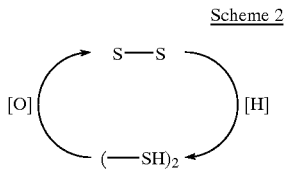

Steps (a) and (b) can be performed in any order. Moreover, as the method can be used to repeatedly switch a mixture between emulsified and non-emulsified states steps (a) and (b) can be performed any number of times.

The method can be used, for example, in improved separation or polymerization processes, where it is desired to change the properties of the mixture to achieve, for example, better flow characteristics, altered surface tensions, and different behavior at liquid-solid and liquid-solid-liquid interfaces. Those of skill will recognize that this unique system provides advantages other than those exemplified above.

In a preferred embodiment, the technique is practiced to recycle the surfactant. This embodiment is unique among cleavable surfactants, as the known cleavable surfactants cannot easily be regenerated. In contrast, the present agents can be readily regenerated by, for example, simple air oxidation, contacting the disulfide with DMSO or Iodine and a variety of other methods for producing disulfides known to those of skill in the art. Reforming the surfactant is preferably performed after the surfactant solution and the other mixture components (e.g., the water-insoluble material) have been separated.

It has now been discovered via the measurement of the time-dependent surface tensions of aqueous solutions during redox-induced transformations of water-soluble surfactants from bolaform (i.e., PRRP, where P is a polar head group and R is a hydrophobic chain) to monomeric, RP, structures that there is a transient decrease in surface tension during the reduction. Whereas past studies have demonstrated that the surface tensions of aqueous solutions measured before and after a redox-induced change in the structure of a surfactant can differ by as much as 23 mN/m (electrochemical oxidation and reduction of ferrocene-based surfactants in aqueous solution can lead to large and reversible changes in surface tension, the time-dependent evolution of the surface tension during the transformation was not investigated (Gallardo et. al., *Langmuir* 11: 4209–4212 (1995); Bennett et al., *J. Am. Chem. Soc.* 118: 6499–6505 (1996); Gallardo et al., *Langmuir* 12: 4116–4124 (1996)). Other studies have demonstrated that contacting a natural acid-containing crude oil phase and an alkaline aqueous phase can give rise to transient minima in oil/water interfacial tensions (see, for example, Rubin et al., *Chem. Eng, Sci.* 35: 1129–1138 (1980); Rudin et al., *Ind. Eng. Chem. Res.* 33: 1150–158 (1994), and references therein).

Surface tensions measured during redox-induced transformations of bolaform surfactants to monomeric ones can be substantially lower (~10 mN/m) than the initial or final equilibrium (i.e., in the absence of an ongoing chemical reaction) surface tensions of the system and that the extent of lowering of the surface tension is dependent upon the rate of the redox-induced transformation of PRRP to RP. These observations suggest that redox-induced transformations of surfactants can be exploited to manipulate (transient) surface tensions.

Thus, in another aspect, the invention provides a method for producing a transient reduction in the surface tension of a solution or emulsion comprising a disulfide-containing surfactant of the invention. The method comprises contacting the surfactant with a reducing agent. Substantially any reducing agent capable of cleaving a disulfide moiety is useful in this aspect of the invention, however, dithiothreitol and $Na_2SO_3$ are currently preferred.

Although essentially any substantially water-soluble surfactant that contains a reducible disulfide group can be used to practice the present invention, in a preferred embodiment, the surfactant has a structure according to Formula (I), preferably Formula (II), more preferably Formula (III) and still more preferably Formula (IV).

It has also been discovered that changes in the pH of the surfactant solution during the reduction of a disulfide-containing surfactant can exert a significant effect (up to ~10 mN/m of a change of about ~3 pH units) on the surface tension of the solution. Moreover, it is known that protons can be produced and destroyed at an electrode in a reversible reaction, thereby providing an electrochemical means to vary the pH of a solution (see, for example, Bard et al., Electrochemical Methods: Fundamental and Applications, John Wiley and Sons, New York, 1980).

Thus, in yet a further aspect, the present invention provides a method of electrochemically manipulating surface tension of aqueous solutions of disulfide surfactants. The method comprises applying either a reducing or oxidizing potential to the solution of the surfactant to produce or destroy protons, thereby altering the surface tension of the solution.

In one preferred embodiment, the aqueous solution is a component of an emulsion. In another preferred embodiment, the surface tension is altered by about 1 mN/m to about 15 mN/m.

Improved Surfactant Properties

The methods set forth above are possible to carry out, because of the surprisingly improved properties of the chemodegradable surfactants of the invention. Past studies of chemodegradable surfactants have employed the use of various functional groups (e.g., acetal, siloxane, azo, and disulfide) that can be transformed by adjustment of pH, exposure to light, or other chemical means (e.g., by addition of a chemical reducing agent) (see, Table 1). However, chemodegradable surfactant systems investigated in the past combine relatively few of the properties necessary in a chemodegradable surfactant.

For a chemodegradable surfactant to be accepted and widely used in research, industrial and waste treatment applications, candidate molecules must meet certain criteria. First, the surfactant must be inexpensive to synthesize. Thus, the incorporation of a chemodegradable group into a surfactant structure should not unduly complicate the synthesis of the surfactant. Moreover, the structure of the surfactant and the chemical reactions used to arrive at this structure must be flexible enough to permit the incorporation of a variety of types hydrophobic tails and polar head groups into surfactant structures (e.g., cationic, anionic, nonionic head groups).

Second, the chemodegradable surfactants should be approximately as surface-active as their non-chemodegradable analogues. Thus, the solution properties of chemodegradable surfactants should not be compromised, prior to their transformation into surface-inactive states, relative to classical surfactants. Useful agents will produce solutions having surface tensions of from about 30 mN/m to about 55 mN/m.

Moreover, chemodegradable surfactants must be water-soluble and stable under ambient conditions (e.g., upon exposure to air, a broad pH range, and the presence of light) so that their use does not require a restrictive level of control over solution conditions (e.g., pH). Useful agents will be sufficiently soluble to produce at least a 0.1, preferably a 1 mM solution and more preferably a 2 mM solution in water and they will be stable over a pH range of from about 3 to about 11, undergoing less than about 80% degradation after about 24 hours in solution. The combination of solubility and stability allows the present surfactants to be used in a broad range of procedures and under variable conditions.

Additionally, the transformation of the chemodegradable surfactant from its surface-active to surface-inactive state must be possible without requiring a large excess of a transforming reagent. Whereas past studies have reported the design of surfactants that degrade to surface-inactive products in the presence of excess acid or base, a transformation involving the addition of a near-stoichiometric amount of a transforming agent eliminates the need for subsequent steps such as the neutralization of excess acid or base prior to disposal (streams of effluent wastewater are regulated by the Environmental Protection Agency (EPA) to be released between pH 6–9; see, Corbitt, *Standard Handbook of Environmental Engineering*, McGraw-Hill, Inc.: New York, (1990) p. 3.11)). Also, in applications involving proteins and other biological molecules, extremes in pH (excess acid or base) often lead to the irreversible loss of structure and function. Thus, useful surfactants will be cleaved under conditions using less than about five equivalents of cleavage reagent per disulfide group.

Finally, in order for the chemodegradable surfactant to be broadly accepted, the transformation from its surface-active state to its surface inactive state must occur quickly after the addition of the transforming reagent. Useful agents are those that undergo at least 70% cleavage in less than about 6 hours.

The present agents meet each of the above criteria. The compounds are synthesized from inexpensive, readily available precursors and the surfactants are assembled in high yield using only a few steps (e.g., nucleophilic mono-substitution of a dihaloalkane with thiolactic acid to produce a thioacetate, conversion of the thioacetate to the thiol via transesterification and formation of the quaternary ammonium derivative by nucleophilic substitution using a trialkylamine). In this particular exemplary synthetic pathway, the availability and low cost of the dihaloalkyl precursors allows a wide range of non-polar "tail" groups to be incorporated into the surfactants. Moreover, the simplicity and predictability of the nucleophilic substitution reaction, allows the introduction of a wide range of polar head groups into the molecule.

The surfactants of the invention are also highly water soluble and solutions having a concentration of 10 mM and greater are easily prepared. The agents are also stable under a range of solution conditions (e.g., from pH 3–11 for 24 hours). The surfactants are also highly surface active. For example, a solution of surfactant 1 has surface tension limiting values of approximately 45 mN/m at a concentration of 10 mM.

A review of known chemodegradable surfactants motivates the conclusion that, unlike the surfactants of the present invention, none of these known surfactant systems meet each of the criteria set forth above. For example, past studies of acid-labile surfactants (Jaeger, *J. Org. Chem.* 58: 2619–2627 (1993); Masuyama, et al., *J. Jpn. Oil Chem. Soc.* 44: 446–450 (1995); Piasecki, et al., *Langmuir* 13: 1434–1439 (1997); Jaeger et al.,. *Langmuir* 14:1940–1941 (1998); Kida et al., Y. *J. Am. Oil Chem. Soc.* 71: 705–710 (1994); Jaeger et al., *Langmuir* 12, 4314–4316 (1996); Ono et al., *J. Org. Chem.* 55: 4461–4464 (1990)), (see, Table 1) have reported both low values of limiting surface tensions (~25.1 mN/m) and changes in surface tension of ~21 mN/m upon hydrolysis (Masuyama, supra, (Yue et al., *J. Am. Oil Chem. Soc.* 73: 841–845 (1996); Burczyk et al., *J. Am. Oil Chem. Soc.* 74: 895 (1997))).

Despite the characteristics of both the intact and degraded hydrolytically-sensitive surfactant, the hydrolytic cleavage of acid-labile surfactants requires high concentrations of acids that lead to low pHs (e.g., pH 1). Similarly, base-labile surfactants (Jaeger et al., *J. Org. Chem.* 51: 3956–3959 (1986); West et al., *Tetrahedron Lett.* 51: 9135–9138 (1996);. Lindstedt et al., *Antimicrob. Agents Chemother.* 34: 1949–1954 (1990)), (see, Table 1) have required the addition of large concentrations of bases that result in solutions having an unacceptably high pH (e.g., pH 13). As discussed above, the required excess of acid or base is undesirable for several reasons, including the need to neutralize the solution prior to its disposal. The use of weak acids and bases has also been reported, thus avoiding extremes in pH. However, reaction times for these hydrolyses are unacceptably long (up to ~48 h) (West, supra).

In contrast to the acid and base labile surfactants, the present surfactants are quantitatively cleaved within about three minutes using no more than 5 equivalents of a cleavage reagent.

Past studies have also investigated chemodegradable surfactants that can be transformed by chemical means other than by changing pH (see, Table 1). Examples include the ozonolysis of carbon-carbon double bonds in surfactant structures (Masuyama, supra). The ozonolysis of the surfactant was reported to occur rapidly (within 5 min). However, an additional chemical reaction was required to form stable degradation products in water (i.e., sodium borohydride was added to stabilize a,a'-dihydroxyperoxides formed by ozonolysis). In contrast, the present surfactants, form stable solutions upon oxidation and do not require a second reaction to stabilize them or their solutions.

Surfactants that use photodegradative, rather than chemodegradative, pathways are known, however, these compounds are also less than ideal cleavable surfactants. The surface tensions of aqueous solutions of surfactants containing the photosensitive azo (N=N) moiety have been reported to be low (~28 mN/m) and to increase by ~32 mN/m upon illumination of the solution with UV light (Dunkin et al., *J. Chem. Soc., Perkin Trans.* 29: 1837–1842 (1996)), (see, Table 1). These transformations (involving the cleavage of the azo linkage), however, are unacceptably long, being reported to occur over approximately 15–21 h. Thus, although photosensitive surfactants can comprise a surfactant system transformable between two states, complete photolysis of these surfactants is very slow. Moreover, precautions must be taken to store these surfactants in the absence of ambient light.

In contrast, the present surfactants needn't be protected from light and, as discussed above, are much more rapidly cleaved than the photolabile surfactants.

Past investigations of chemodegradable surfactants have not identified systems that combine the properties desired in a chemodegradable surfactant system. In contrast, the present invention provides new chemodegradable surfactant systems based on oxidation of the disulfide-based surfactant $(1=Br^-N^+(CH_3)_3(CH_2)_8SS(CH_2)_8N^+(CH_3)_3Br^-)$ to intermediate oxidation products (e.g., disulfoxide, disulfone) and sulfonate fragments $(5=N^+(CH_3)_3-(CH_2)_8-SO_3^-)$ by using sodium hypochlorite (NaOCl) (see, FIG. 11).

This chemodegradable surfactant system possesses three advantages over prior systems. First, because the disulfide bond is hydrophobic, it can be incorporated within a hydrocarbon chain without substantially perturbing the hydrophobic nature of the chain. Thus, the interfacial properties of solutions of 1 are similar to those of the bolaform surfactant $Br^-N^+(CH_3)_3(CH_2)_{16}N^+(CH_3)_3Br^-$ (see, FIG. 11). Second, disulfide bonds can be readily oxidized (see FIG. 12) upon the addition of stoichiometric amounts of NaOCl under mild conditions (25° C.). Third, the oxidation products of disulfides (such as the disulfoxide (—SO—SO—), sulfone (—SO$_2$—SO$_2$—), or sulfonate (—SO$_3^-$)) are more hydrophilic than the disulfides. Therefore, the oxidation of 1 leads to large changes in the amphiphilic nature of the molecule or its fragments and, thus causes large changes in the surface tensions of aqueous solutions of 1.

The materials and methods of the present invention are further illustrated by the examples which follow. These examples are offered to illustrate, but not to limit the claimed invention.

EXAMPLES

Example 1

This example illustrates the synthesis of the surfactants bis(8-trimethylammonium bromide)dioctyl disulfide (1) and (8-mercaptooctyl)trimethylammonium bromide (2).

1.1 Synthesis of bis(8-Trimethylammonium Bromide) dioctyl Disulfide (1)

A solution of 8-bromo-1-octanethiol (0.7 g, 3.1 mmol) in 20 mL ethanol was titrated with a 65 mM solution of iodine in ethanol (~23 mL) until a light yellow color persisted (Bain, C. D. et al., *Langmuir*, 5:723–727. (1989). The ethanol was removed at 40° C. by rotary evaporation, The dark-maroon colored oil was dissolved in 40 mL ether and extracted with distilled water (4×50 mL). The ethereal layer was dried over anhydrous sodium sulfate and the solvent removed under vacuum at 30° C. Flash chromatography (80:20 hexanes:methylene chloride) afforded di(8-bromooctyl)disulfide, a yellowish oil, in 80% yield, $^1$H NMR (CDCl$_3$) δ 3.41 (t, 4H), 2.68 (t, 4H), 1.86 (m, 4H), 1.67 4 m H), 1.20–1.50 (m, 16H).

Di(8-bromooctyl)disulfide (0,3 g, 0.7 mmol) and an excess amount of trimethylamine in 4.2 M ethanolic solution (0.3 g, 2 mmol) were added to a degassed solution of ethyl acetate (10 mL). The mixture was stirred under nitrogen at room temperature for 12 days, during which time bis(8-trimethylammonium bromide)dioctyl disulfide precipitated out of solution as a white solid. The solid was washed with ethyl acetate (3×5 mL) and hexanes (3×5 mL). Between washings, the solid was recovered using a centrifuge (3500 rpm, 15 min intervals) while the spent solvent was decanted. The solid (95% yield) was dried under vacuum and stared under nitrogen. This hygroscopic compound was handled under nitrogen: $^1$H NMR (CDCl$_3$) δ 3.79 (m, 2H), 3.64 (m, 2H), 3.45 (s, 18H), 2.70 (m, 4H), 1.75 (m, 4H), 1,67 (m, 4H), 1.20–150 (m, 16H). Anal. Calcd for $C_{22}Hr_{50}Br_2N_2S_2$: C, 46.67; H, 8.89; Br, 28.21; N, 4.94; S, 11.32. Found: C, 44.87; H, 8.95; Br, 27.48; N, 4.53; S, 11.30.

1.2 Synthesis of (8-Mercaptooctyl)trimethylammonium Bromide (2)

1,8-dibromooctane (4.0 g, 14.7 mmol) was added to a degassed solution of methanol (275 mL) in a 500-mL three-neck flask. A sodium methoxide solution, prepared by reacting sodium metal (0.3 g, 14.7 mmol) in methanol (degassed, 120 mL) and cooled over an ice bath, was mixed with thiolacetic acid (1.16 g, 14.7 mmol) and transferred to an addition funnel. The solution in the three-neck flask was refluxed under nitrogen for 4.5 h, during which time the contents of the addition funnel were added dropwise. After cooling the solution to room temperature, the solvent was removed by rotary evaporation. Flash chromatography of the yellow oil (96:4 hexanes:ethyl acetate) yielded 1.5 g of 8-bromo-1-octyl thioacetate (Troughton, E. B. et al., *Langmuir*, 4:365–385 (1988) as a colorless ail.

8-bromo-1-octyl thioacetate was converted to 8-bromo-1-octanethiol by transesterification using dry hydrochloric acid in methanol (Bain, C. D, et al.; *J. Am. Chem Soc.* 111:321–335 (1989). Flash chromatography (80:20 hexanes: methylene chloride) yielded 8-bromo-1-octanethiol as a colorless oil (75% yield): $^1$H NMR (CDCl$_3$) δ 3.40 (t, 2H), 2.50 (q, 2H), 1.84 (m, 2H), 1.58 (m, 2H), 1.20–1.50 (m, 9H).

8-bromo-1-octanethiol (0.4 g, 1.8 mmol) and an excess amount of trimethylamine in 4.2 M ethanolic solution (0.38 g, 2.2 mmol) were added to a degassed solution of ethyl acetate (15 mL). The mixture was stirred under nitrogen at room temperature for 10 days, during which time (8-mercaptooctyl)trimethylammonium bromide precipitated out of solution as a white solid. The solid was washed with ethyl acetate (3×5 mL) and hexanes (3×5 mL). Between washings, the solid was recovered using a centrifuge (3500 rpm, 15 min intervals) while the spent solvent was decanted. The solid (80% yield) was dried under vacuum and stored under nitrogen: $^1$H NMR (CDCl$_3$) δ 3.60 (m, 2H), 3.47 (s, 9H), 2.53 (q, 2H), 1.76 (m, 2H), 1.62 (m, 2H), 1.20–1.50 (m, 9H). Anal. Calcd for $C_{11}H_{26}BrNS$: C, 46.47; H, 9.22; Br, 28.11; N, 4,93; S, 11.28. Found: C, 46.83; H, 9.50; Br, 27.81; N, 4.96; S, 11.34.

Example 2

This example demonstrates the measurement of the time-dependent surface tensions of aqueous solutions during redox-induced transformations of water-soluble surfactants from bolaform (PRRP, where P is a polar head group and R is a hydro-phobic chain) to monomeric (RP) structures. This example is based on measurements of surface tension during the reduction of a disulfide-containing, bolaform surfactant (1) to less surface-active monomeric, thiol-containing fragments (2).

2.1 Materials and Methods

Figure 2:
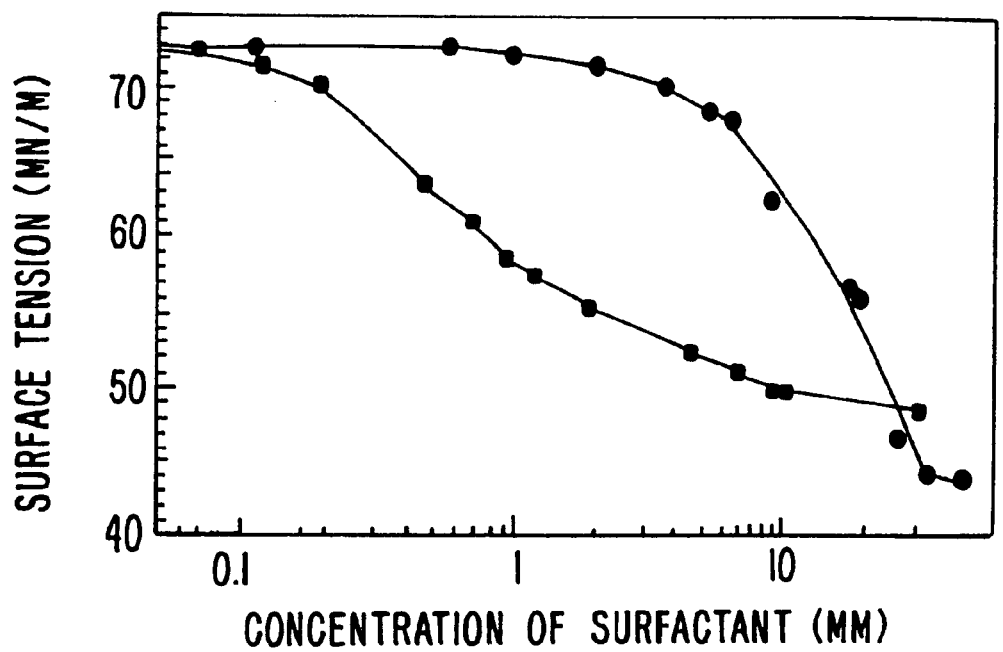
FIG. 2. Graphic representation of measurements of surface tension versus concentration of surfactant for aqueous solutions (50 mM phosphate buffer, 25° C., pH 6.9) of 1 (■) and 2 (●).

Surfactants 1 and 2 (FIG. 1) were synthesized according to procedures described in Example 1. FIG. 2 shows surface tensions of aqueous solutions (50 mM phosphate buffer, pH 6.9, deoxygenated) of 1 and 2 measured by using a maximum bubble pressure tensiometer (SensaDyne, Mesa, Ariz.) bubbled at 01–0.3 Hz and 25° C. (Menger, F. M. et al., *J. Am. Chem. Soc.* 115:10083–10090 (1993)). Surface tensions measured at bubble frequencies less than 0.1 Hz were similar to those measured at 0.1 Hz. The surface tensions of the reacting system reported herein correspond, therefore, to a local steady state at the surface of the solution. In the absence of reaction, these surface tensions are equilibrium tensions.

2.2 Results

The threshold concentration of surfactant causing a measurable reduction in surface tension was found to be an order of magnitude lower for 1 (~0.1 mM) as compared to 2 (~1 mM). Reduction of 1 to 2 leads to changes in surface tension of up to 17 mM/m. Because the average area occupied by 1 at the surface of a 1 mM solution of 1 is estimated to be 117 Å$^2$/molecule whereas the average area occupied by 2 at the surface of a 2 mM solution of 2 is estimated to be >500 A$^2$/molecule (the molecular areas were estimated by using the Gibbs adsorption equation in the presence of swamping concentrations of electrolyte and by assuming ideal solution behavior in the bulk of the solution. The overall increase in surface tension upon reduction of 1 to 2 is apparently caused by desorption of surfactant from the surface of the solution. Dimeric, trimeric, and polymeric surfactants that possess disulfide bonds can, we believe, provide the capability to effect large changes in surface tension over wide ranges of concentration (see, for example, Gallardo et al. *Langmuir* (1997 13:203–208.))

Rates and equilibria of redox reactions involving thiols and disulfides have been measured in past studies of the autoxidation of cysteine-containing enzymes, protein folding, and the pharmacological and therapeutic actions of a number of drugs (Szajewski et al., *J. Am. Chem. Soc.* 102: 2011–2026 (1980); Gilbert, H. F., *Adv. Enzymol.* 63: 69–172 (1 990); Kim et al., *Annu. Rev. Biochem.* 59: 631–660 (1990); Woghiren et al., *Bioconjugate Chem.* 4: 314–318 (1993)). Thiol-disulfide exchange is abase-catalyzed, $S_N^2$ displacement reaction in which the thiolate anion RS$^-$ is the nucleophile. (Singh et al., in *The Chemistry of the Thiol Group, Supplement*; Patai et al. Eds.; Wiley: New York, 1993.) Measurements were obtained of the rate of change of surface tension caused by thiol-disulfide exchange between DTT and 1; the exchange process results in formation of 2 and oxidized DTT. DTT was used in this experiments for four reasons: (i) DTT is a strong reducing agent (Cleland, W. W., *Biochemistry* 3: 480–482 (1964); Jocelyn, P. C., *Methods Enzymol.* 143: 246–256 (1987)) and thus the equilibrium lies toward 2 (Whitesides et al., *J. Org. Chem.* 42: 332–338 (1977)); (ii) the formation of mixed disulfide products (HS—R$_3$—S—S—R$_1$) is small because oxidized DTT is a stable, cyclic disulfide (Whitesides et al., *J. Org. Chem.* 42: 332–338 (1977)); (iii) DTT and oxidized 3 are not surface-active (the addition of 10 mM DTT and 1 mM oxidized DTT to water did not result in a change in surface tension); and (iv) DTT has been reported to reduce water-insoluble, disulfide-containing lipids leading to the rupture of lipid membranes. (Ringsdorfet al., *Angew, Chem., Int. Ed. Engl.* 27: 113–158 (1988)).

Figure 3:
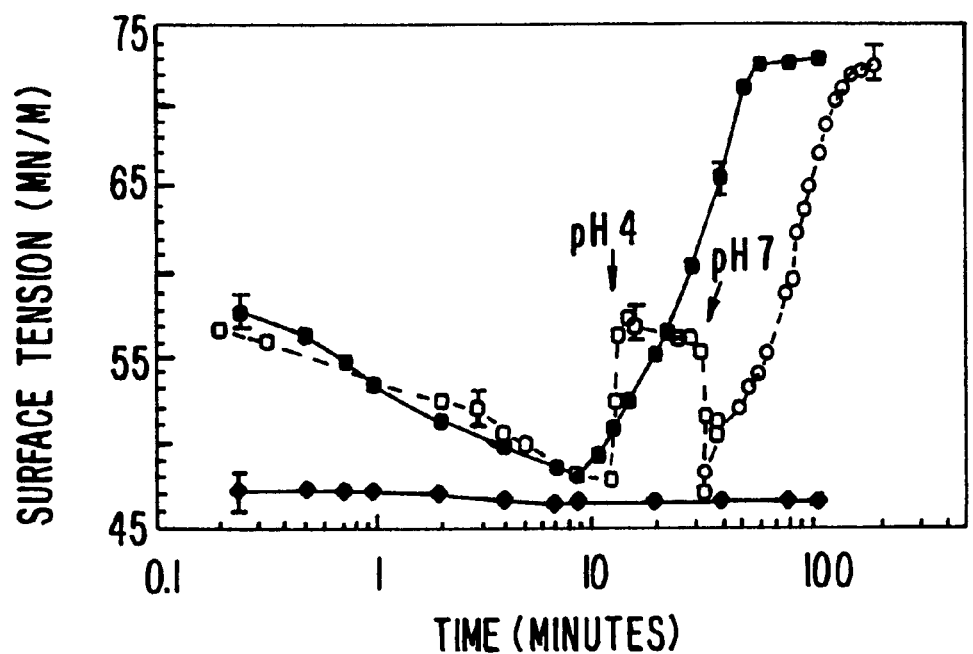
FIG. 3. Graphic representation of measurements of surface tension versus time for aqueous solutions (50 mM phosphate buffer at 25° C.) of 1 mM of 1 following the addition of DTT at pH 6.9 (●); 20 mM of DTT with step change in pH from 6.9 to 4.0 (phosphoric acid) to 7.0 (sodium hydroxide) (○). Also shown is the surface tension of a 1 mM solution of CTAB following the addition of 10 mM of DTT (▲).

FIG. 3 (filled circles) shows measurements of the surface tension of aqueous solutions of 1 (1 mM, pH 6.9) following the addition of DTT (20 mM). The surface tension of a 1 mM solution of 1 was initially 57 mN/m. Approximately 10 min after the addition of DTT, however, the surface tension decreased by ~10 mN/m even though the product of the exchange reaction was confirmed to be species, 2, a species that is less surface active than 1. The product of reduction was identified as 2 by using thin-layer chromatography (aluminum oxide plates, methanol as eluent). As the exchange reaction progressed, the surface tension passed through a minimum. At the completion of the reaction, the surface tension of the solution was 72 mN/m (i.e., surface tension of a solution of 2). Both the overall rate of reduction of 1 to 2 and the magnitude of the transient reduction in surface tension were observed to change with the concentration of DTT. The addition of acid which is known to quench thiol-disulfide exchange reactions by protonation of the thiolate anion (Krisovitch. et al., *J. Am. Chem. Soc.* 114: 9828–9835 (1992)), was observed to cause an abrupt (and reversible) increase in surface tension followed the addition of DTT to a solution of cetyltrimethylammonium bromide (CTAB).

Two additional observations led to the conclusion that the minimum in surface tension measured during the reduction of 1 to 2 is not an equilibrium property of a mixture containing 1 and 2 and is not a result of the surface activity of DTT, oxidized DTT, or intermediate chemical species (e.g., HS—$R_3$—S—S—$R_1$) First, the surface tensions of all solutions prepared by directly mixing 1 and 2 (not reacting) were greater than those for 1 alone (FIG. 3). That is, the so-called "synergism" of surfactant mixtures (Rosen, M. J. *Surfactants and Interfacial Phenomena*, $2^{nd}$ ed.; Wiley: New York) does not explain these results. Second, the minimum in surface tension was observed when 1 was reduced to 2 by the using either $Na_2SO_3$ or DTT. Therefore, the transient lowering of surface tension is not likely to be caused by the presence of intermediate chemical species such as unsymmetrical disulfides formed during the reduction of 1 to 2 using DTT.

Figure 4:
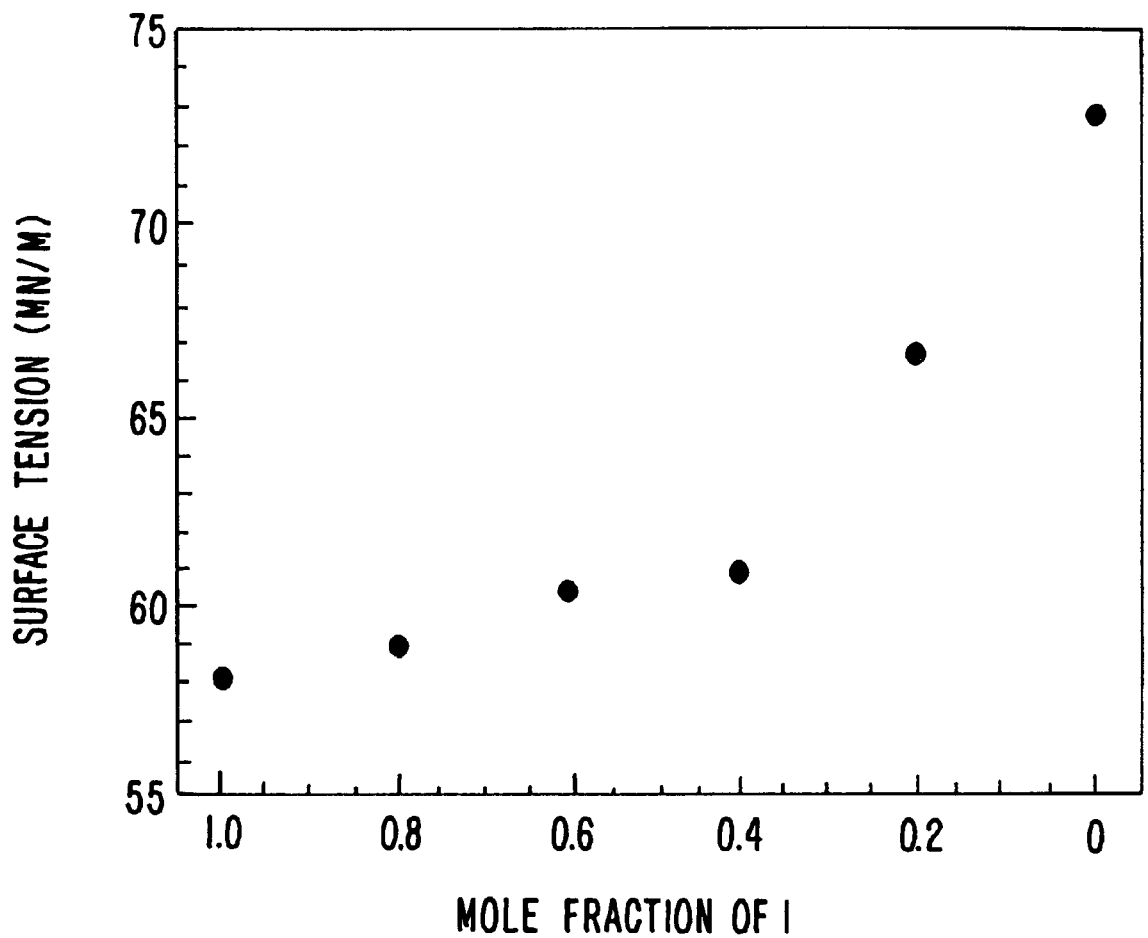
FIG. 4. Graphic representation of surface tension versus mole fraction of surfactant 1.

The results presented in FIG. 3 and FIG. 4 demonstrate that the surface tensions measured during reduction of 1 to 2 are substantially lower than surface tensions of nonreacting mixtures corresponding to the same composition of the bulk solution. Therefore, the low surface tensions measured during the reduction of 1 to 2 arise from nonequilibrium surface states created by the transformation of a bolaform surfactant to a monomeric structure. It is hypothesized that the low, transient surface tensions measured during the reduction of 1 to 2 are caused by a transient surface excess concentration of surfactant (1 and 2) that is greater than the equilibrium value corresponding to the instantaneous bulk composition of the solution. This situation can arise if the rate of reduction of 1 to 2 within the surface monolayer is greater than the rate at which 2 desorbs from the surface of the solution. It is likely that a barrier to desorption of 2 from the surface of the solution leads to the accumulation of 2 at the surface of the solution. This hypothesis is supported by preliminary results of a diffusion-kinetic model (Rubin, et al., *J. Chem. Eng. Sci.* 35:1129–1138 (1980); Rudin et al., *Ind. Eng. Chem. Res.* 33: 1150–1158 (1994), and references therein) and by the observation that a 1 mM solution of 1 has a surface excess of 0.0085 molecule/Å$^2$ and a surface excess of 2×0.0085 molecule/Å$^2$ can have a surface tension that is less than 57 mN/m (Ahmad, J. *Langmuir* 12: 963–965 (1996)).

Example 3

This example demonstrates the control of the interfacial tension between oil and water utilizing an exemplary surfactant of the invention.

3.1 Materials and Methods

Interfacial tensions were measured by the following procedure. An electronic pipet (Matrix, Lowell, Mass.) with an inverted needle (22 gauge, 1.5-inch bent into a U-shape) was used to form a dodecane bubble with a volume of 5.5 μl which was held over 2 h (during the course of the experiment). The needle was immersed into a cuvette containing a 1 mM solution of 1 and 10 mM DTT. Images of the drop were captured every 10 min (up to 120 min) using a CCD video camera (Sony, New York City, N.Y.). Frames of the images were acquired using commercially available software by (Rasterops Mediagrabber, Westwood, Mass.), and the edge of the bubble was located using Data Thief software. The bubble edge was then numerically compared to the shape predicted by the Young-Laplace equation for a given interfacial tension.

3.2 Results

The reduction of 1,16 bis(trimethylammonium)dibromide dioctyl disulfide (1) to 8-mercaptooctyl trimethylammonium bromide (2) by dithiothreitol (DTT) (FIG. 1) within an aqueous solution in contact with dodecane was demonstrated to lead to a substantial increase in the interfacial tension between the dodecane and the aqueous phase.

Figure 5:
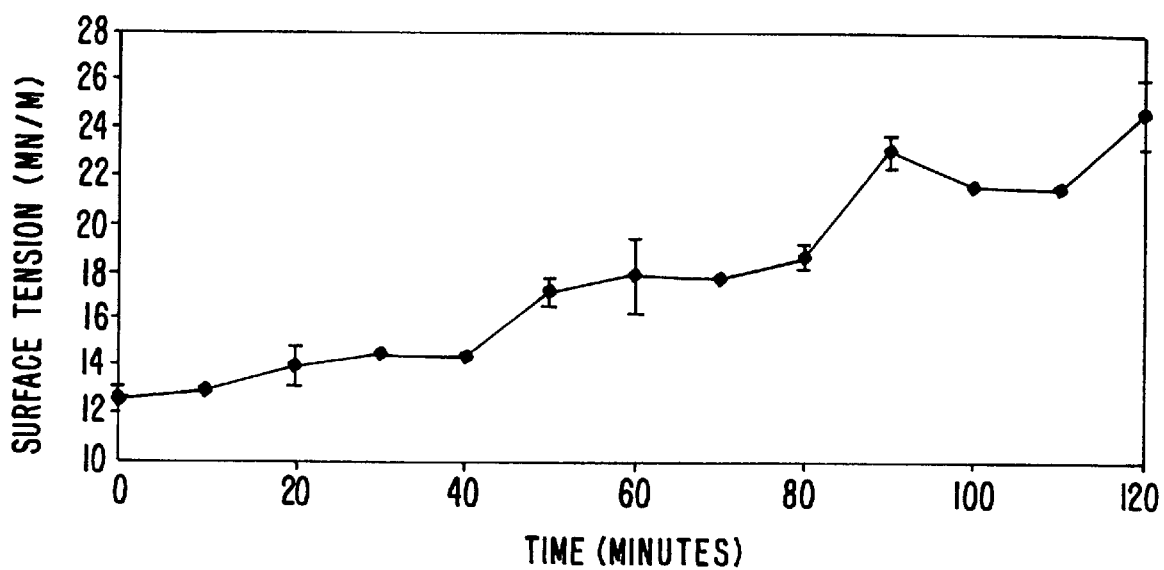
FIG. 5. Graphic display of interfacial tension versus time of a 1 mM solution of 1 undergoing reduction with 10 mM DTT (aqueous phase) in contact with dodecane (oil phase).

The results of these measurements are shown as a function of time of the reaction in FIG. 5. Initially, the interfacial tension of a 1 mM solution of 1 in contact with dodecane was measured to be 12.5 mN/m. Upon oxidation, the interfacial tension increased to a value of 24 mN/m over a period of 2 h.

Example 4

This example demonstrates the control of the stability of emulsions using an exemplary surfactant of the invention. It was demonstrated that reduction of 1,16 bis (trimethylammonium)dibromide dioctyl disulfide (1) to 8-mercaptooctyl trimethylammonium bromide (2) by dithiothreitol (DTT) within an aqueous solution emulsified with dodecane can be used to break the emulsion upon demand.

A 50-Watt High Intensity Ultrasonic Processor (Sonics & Materials, Inc., Newton, Conn.) was used to form an oil-in-water emulsion consisting of 5 wt. % dodecane and a 10 mM solution of 1 in 50 mM phosphate buffer, pH 6.9 (2 mL total). This mixture was sonicated on a setting of 50 for a period of 10 s and then vortexed for 1 min to ensure that the emulsion was thoroughly mixed. No visible change in the appearance of the emulsion (milky color) was observed for >24 h.

Figure 6:
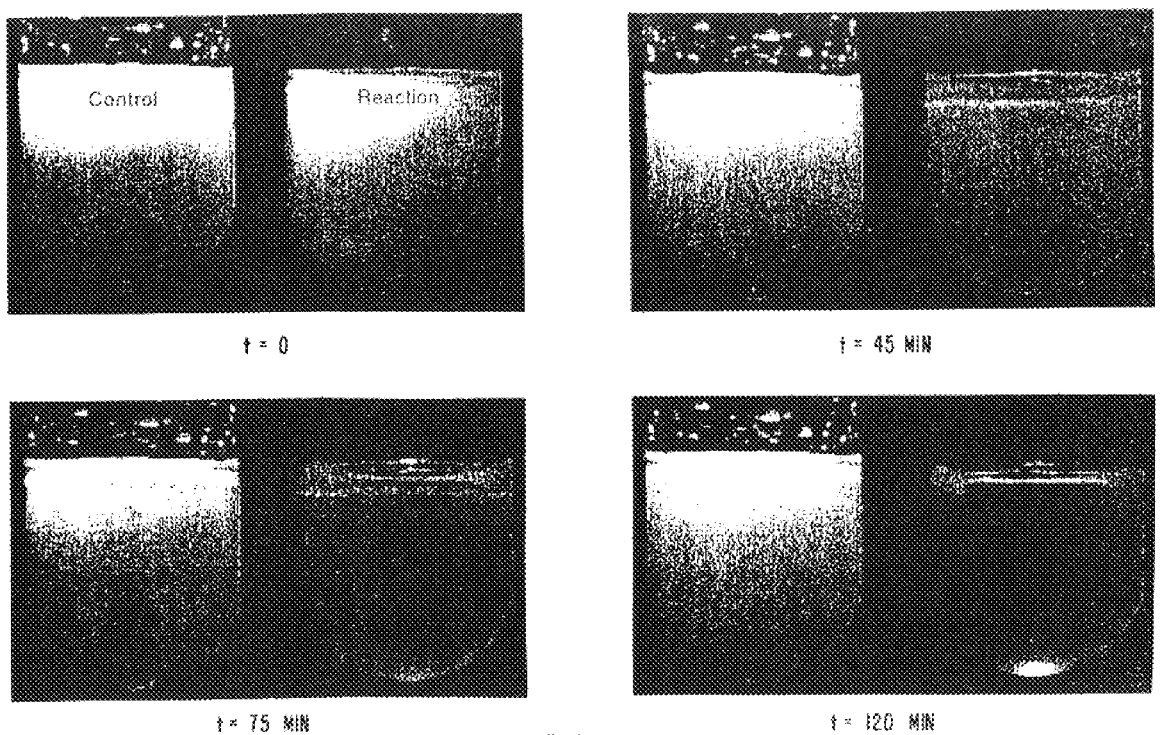
FIG. 6. A series of images demonstrating the disruption of emulsions stabilized by surfactant 1 upon reduction of this surfactant with DTT (100 mM). The emulsions are formed between 10 mM 1 in phosphate buffer and 5% by weight of dodecane.

To a second emulsion prepared in the manner described above was added DTT (10 equivalents) to initiate the reduction of 1. Images of the disruption of emulsions were captured every 15 min over a 120-min period. In contrast to the emulsion to which no DTT was added, addition of DTT caused phase separation of the emulsion starting at ~45 min and reaching completion near 120 min (FIG. 6).

Example 5

This example demonstrates the generality of the surfactants of the invention.

Figure 7:
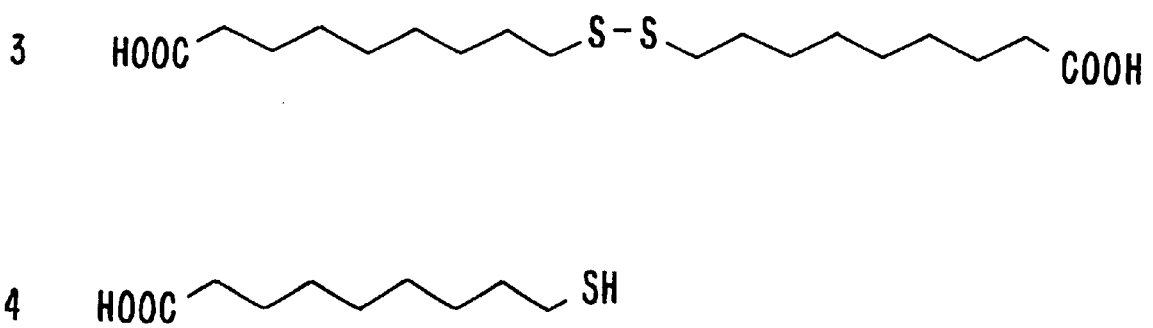
FIG. 7. Structures of exemplary surfactants of the invention 1,16-dicarboxylic dioctyl disulfide (3) and 8-mercaptooctanoic acid (4).
Figure 8:
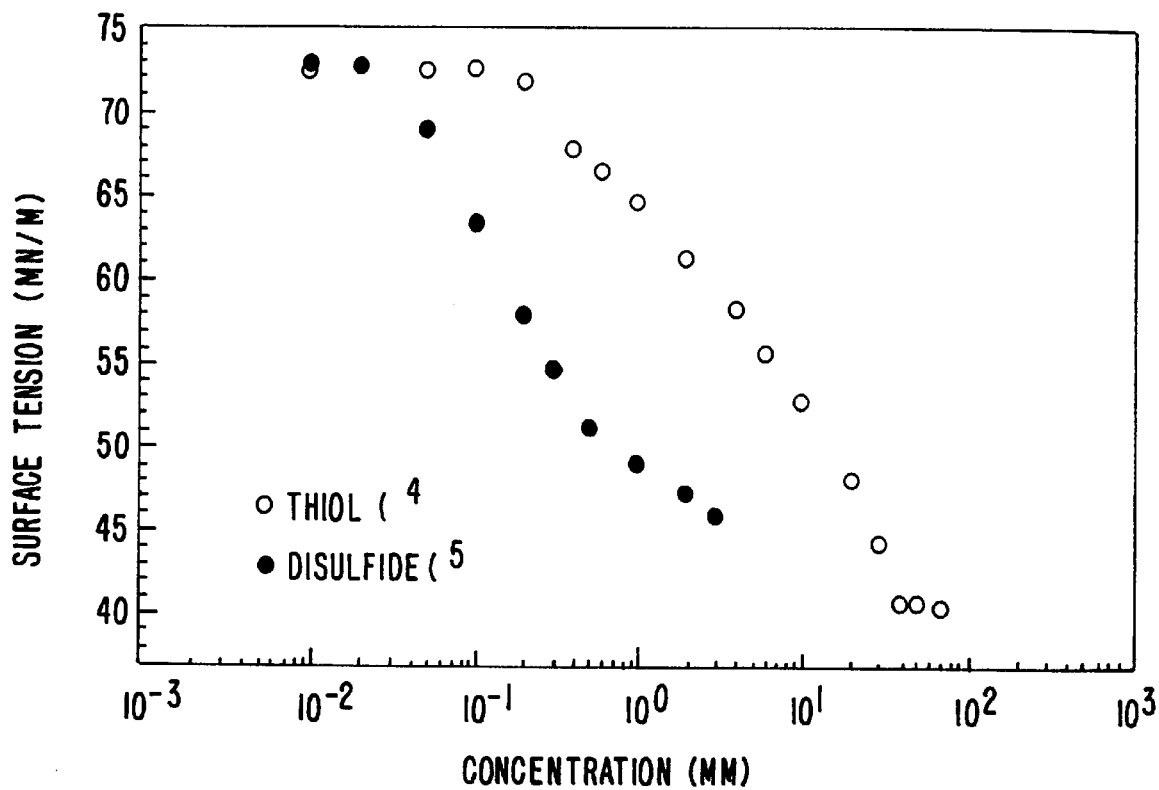
FIG. 8. Graphic representation of equilibrium surface tensions of 3 and 4 in borate buffer (100 mM, pH 9.2).

Disulfide-containing surfactants with anionic head groups were synthesized. FIG. 7 shows the structures of the 1,16 dicarboxylic dioctyl disulfide (3) and 8-mercaptooctanoic acid (4). Equilibrium surface tensions were measured using a Kruss K10T tensiometer with a platinum Wilhelmy plate. Surfactant solutions were prepared in a 100 mM borate buffer, pH 9.2. Glassware was cleaned in piranha solution (70% $H_2SO_4$, 30% $H_2O_2$). The equilibrium surface tension measurements of aqueous solutions containing 3 and 4 are shown in FIG. 8. Differences in surface tensions of up to 16 mN/m between 3 and 4 for a specified concentration are observed, demonstrating that the reduction of 3 to 4 can also lead to large changes in surface tension as observed for the cationic disulfide-containing surfactants 1 and 2.

Example 6

This example demonstrates electrochemical transformations of exemplary surfactants of the invention.

Figure 9:
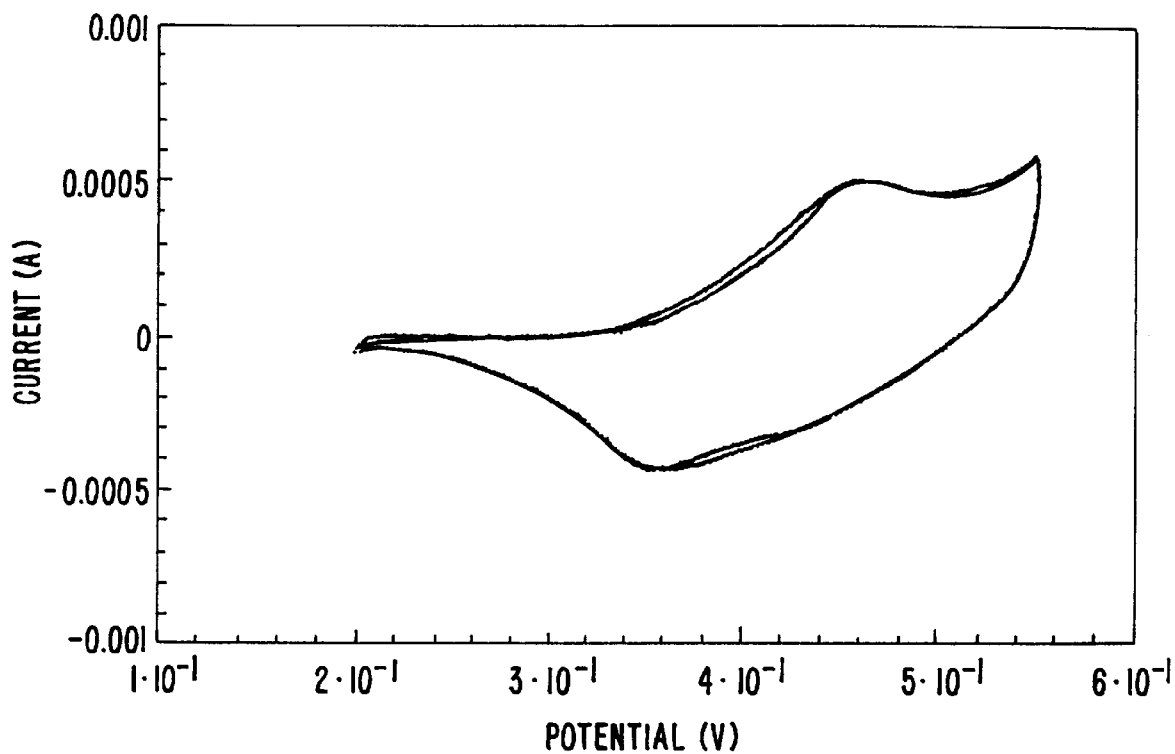
FIG. 9. Plot of current v. potential for 1 in phosphate buffer (50 mM, pH 6.9).
Figure 10:
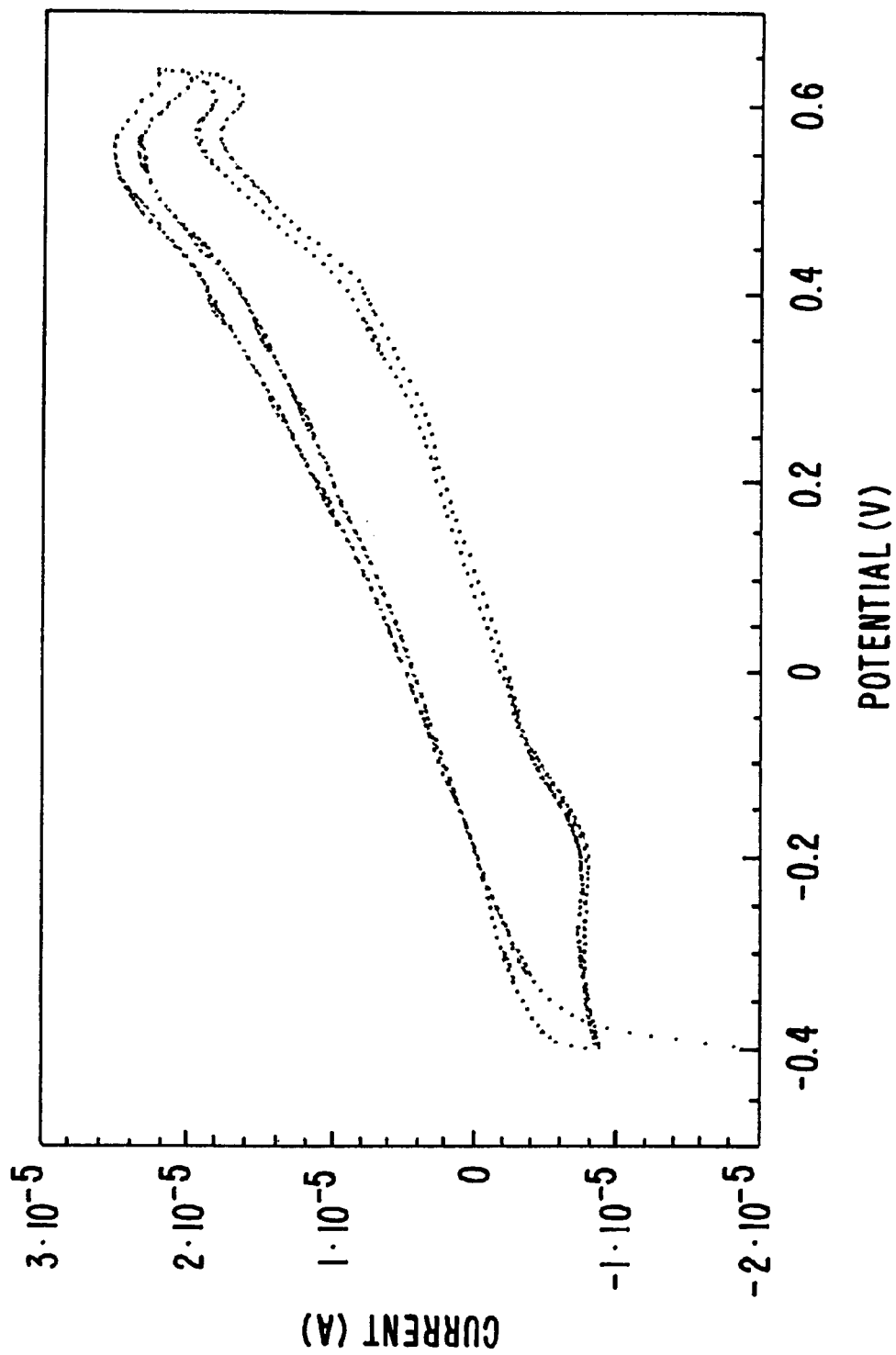
FIG. 10. Plot of current v. potential for 2 in phosphate buffer (50 mM, pH 6.9).

That surfactants 1 and 2 are electrochemically active and thus can be transformed between surface-active and surface-inactive states under electrochemical control has been demonstrated. The cyclic voltammograms of a 5 mM solution of 1 and a 10 mM solution of 2 are shown in FIG. 9 and FIG. 10. Solutions were prepared in 50 mM phosphate buffer, pH 6.9. Application of potential was controlled using a potentiostat (Pine Instruments, Grove City, Pa.), and the experimental set-up involved using a carbon felt working electrode with cobalt phthalocyanine (catalyst) evaporated onto the surface of the electrode. A platinum counter electrode and SCE reference electrode were also used. In the case of the disulfide (1), we observed an oxidation peak at 0.45 V, and a reduction peak at ~0.35 V. In the case of the thiol (2), an oxidation peak was observed at 0.55 V.

Example 7

This Example illustrates the measurement of surface tensions of solutions of compounds 1 and 5.

7.1 Materials and Methods

Solutions of surfactant were prepared in a 50 mM phosphate buffer (pH 6.9). This buffer was made using sodium phosphate (Fisher, Pittsburgh, Pa.) in Milli-Q water (R=18.2 MΩcm, $\gamma$=72.0 mN/m at 25° C.). Glassware was cleaned in piranha solution (18 M $H_2SO_4$, 30% $H_2O_2$, 70:30, v/v). WARNING: Piranha solution should be handled with extreme caution; in some circumstances (most probably when it has been mixed with significant quantities of an oxidizable organic material), it has detonated unexpectedly.

Measurement of Surface Tension

Pendant Drop. Changes in surface tension accompanying the oxidation of 1 were measured using an FTÅ200 pendant drop tensiometer (First Ten Angstroms, Portsmouth, Va.). This instrument captures images of drops or bubbles formed at the tips of needles and analyzes their shapes using the Bashforth-Adams tabulated solution to the Young-Laplace equation. Prior to each set of measurements, the instrument was calibrated with Milli-Q water ($\gamma$=72.6 mN/m at 22° C.). Blunt, stainless steel needles (22 gauge, 1-inch) were made hydrophobic by coating with NyeBar (Nye Lubricants, Inc., New Bedford, Mass.) to prevent drops from climbing up the sides of the needles. NyeBar is composed of perfluoro-containing compounds and is insoluble in water. It was confirmed that the NyeBar coating did not affect measurements of surface tension. (i.e., the surface tension of a 0.2 mM solution of 1 was measured to be 64 mN/m in the presence and absence of the coating on the needle).

The surface tensions of aqueous solutions of 1 were measured by forming a pendant drop of solution at the end of a needle at a rate of 0.5 $\mu$L/s. The total volume of the drop was 6.5 $\mu$L. A new drop was formed for each measurement. Surface tensions were recorded within 1 to 2 min of the formation of the drop, during which time evaporation (lid not measurably affect the size of the drop.

Wilhelmy Plate. Equilibrium surface tensions of aqueous solutions of 1 and 4 were measured using a Kruiss K10T tensiometer with a platinum Wilhelmy plate. Measurements were made at 25° C. using a thermnostated bath. The surface tensions were monitored continuously on a chart recorder. Dewetting of the Wilhelmy plate was not observed during the measurements.

7.2 Results

Figure 13:
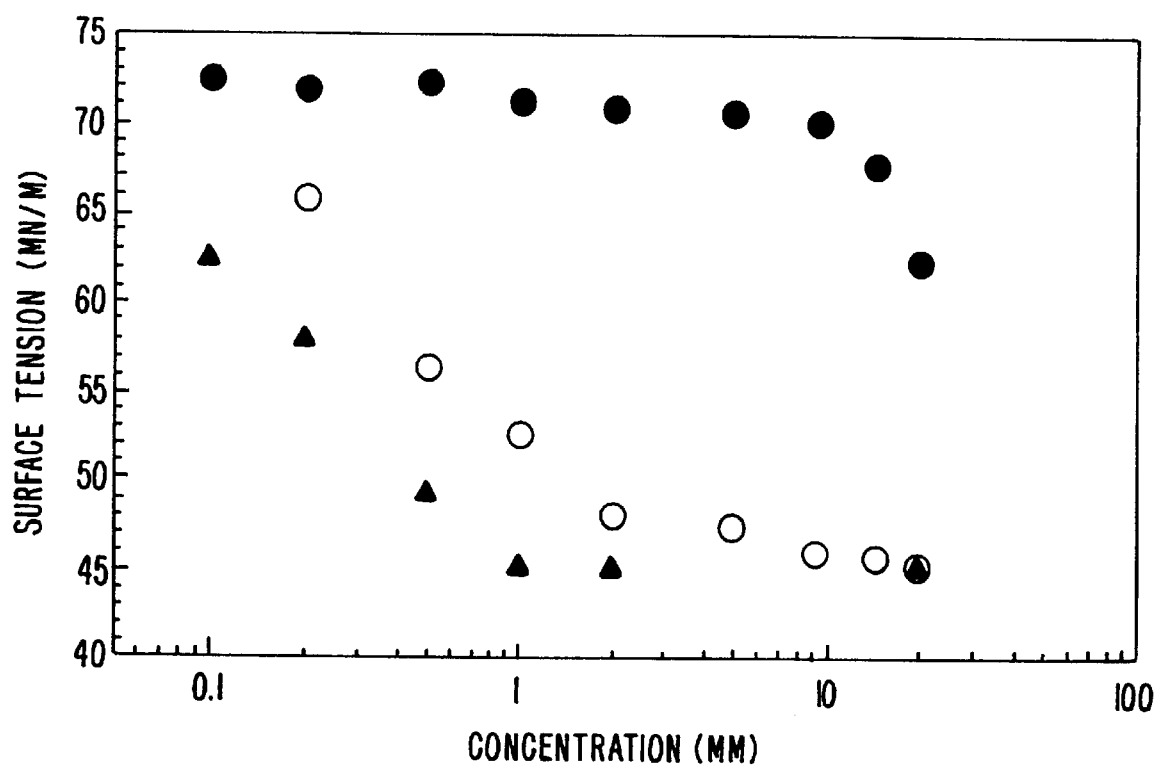
FIG. 13. Surface tensions of aqueous solutions of 1 (50 mM phosphate buffer, pH 6.9) measured using a Wilhelmy plate (▲) and pendant drop (○), and surface tensions of 2 measured using a pendant drop (●).

The surface tensions of aqueous solutions of 1 were measured by using a pendant drop (FIG. 13). The results indicate that 1 measurably reduces the surface tensions of the aqueous solutions of electrolyte at concentrations of 0.1 mM and greater. A limiting surface tension of 45 mN/m was observed at concentrations above 10 mM. Although these measurements were recorded ~1–2 min after the formation of each pendant drop, they do not obviously correspond to the equilibrium values of surface tension. Therefore measurements of equilibrium surface tensions were performed using a Wilhelmy plate. The equilibrium measurements (also shown in FIG. 13 (filled triangles)) were found to be 3–9 mN/m lower than the surface tensions measured when using a pendant drop for concentrations of 1 below 2 mM. Above this concentration, the surface tensions measured by both the pendant drop and Wilhelmy plate technique approached the same limiting value of ~45 mN/m. Because the pendant drop technique permits measurements of time-dependent changes in interfacial properties during the rapid oxidation (~2–3 min) of 1, this method was used to measure surface and interfacial tensions in the investigations of the oxidation of 1.

Figure 14:
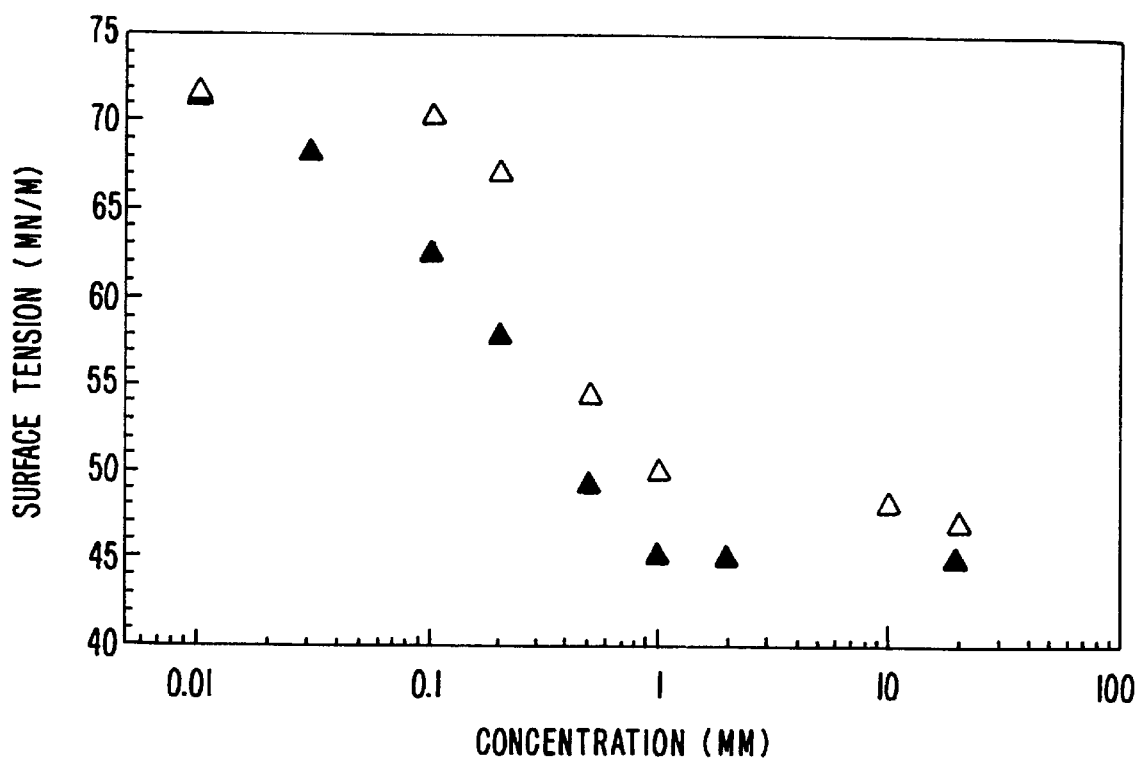
FIG. 14. Surface tensions of aqueous solutions of 1 (▲) and 6 (△) measured using a pendant drop (50 mM phosphate buffer, pH 6.9).

The surface tensions of aqueous solutions of 1 and 4 were compared in order to explore the extent to which the presence of the disulfide bond in 1 perturbs the surface activity of this molecule. The results in FIG. 14 show that the properties of these two surfactants are similar. At low concentrations, the surface tensions of aqueous solutions of 1 are slightly lower (by ~5 mN/m) than those of 4. However, the limiting surface tensions of both solutions of surfactant were found to be within 2 mN/m of each other (~45 mN/m for 1 and ~47 mN/m for 4). These observations suggest that the disulfide bond contributes to the hydrophobic effect that drives the adsorption of surfactants to the surface of the solution. Although the limiting surface tensions of 1 and 4 (~45 mN/m) are not as low as those of classical monomeric surfactants such as cetyltrimethylammonium bromide (e.g., $\gamma_{lim}$ of CTAB=39 mN/m in 0.1 M lithium sulfate) this does not appear to be a general limitation of bolaform surfactants. For example, the limiting surface tensions of bolaform surfactants with shorter chain lengths such as dodecane-1, 12-bis(trimethylammonium dibromide) have been reported to be 38 mN/m when dissolved into water (Menger et al., *J. Phys. Chem.* 78: 1387–1390 (1974). The principal conclusion here is that the presence of the disulfide bond in 1 does not cause its surface activity to differ greatly from that of 4. This observation suggests that structure-property relationships known for classical surfactants can be applied toward the design of chemodegradable surfactants that are based on the use of disulfide bonds.

Example 8

The stability of 1 was investigated and this compound was found to be stable in solid form when stored inside a sealed container at ambient temperatures for >1 yr. When exposed to ambient humidity, the compound was hygroscopic. When dissolved in aqueous solutions, we measured the surface tensions of 2 mM solutions of 1 to remain constant at 48 mN/m (within ~1 mN/m) under ambient conditions (room temperature, exposed to air/light) and at three different pHs (pH 3, 6.9 and 11) for at least 24 h. After 5 days, the surface tensions of solutions of 1 at pH 3 and pH 6.9 increased by ~2 mN/m to 50 mN/m, while the surface tension of the solution at pH 11 increased by 1 mN/m to 49 mN/m. The stability of 1 in solution was comparable to that of CTAB, where the surface tension of a 1 mM solution of CTAB in 50 mM phosphate buffer (pH 6.9) was found to be ~41 mN/m. The surface tension of the solution of CTAB increased by ~0.5 mN/m over a period of 24 h and increased by 1 mN/m over a period of 5 days.

Example 9

This example demonstrates that the oxidation of compound 1 results in an increase in the surface tension of a solution that is consistent with an increase in hydrophilicity of the species in solution.

9.1 Materials and Methods

The concentration of hypochlorite ($OCl^-$) in solution was determined by iodometry (Rosen, et al., *J. Am. Oil Chem. Soc.* 69: 667–671 (1992); Kolthoff et al. *Textbook of Quantitative Inorganic Analysis*, MacMillan: New York, 1945). Briefly, a 5 mL sample containing hypochlorite was diluted with 20 mL of Milli-Q water in a 250-mL Erlenmeyer flask. 2 g KI and 10 mL of 1 N $H_2SO_4$ were added to the solution. The solution was titrated with a standard 0.1 M sodium thiosulfate solution.

A control experiment confirmed that 1 did not interfere with the iodometric determination of hypochlorite in solution. By using iodometry, we determined the concentration of the NaOCl stock solution purchased from Aldrich to be 0.5 M. The concentration of NaOCl in the commercial bleach (which contains ~95% of other "inert ingredients") was also determined to be 0.5 M.

9.2 Results

Figure 15:
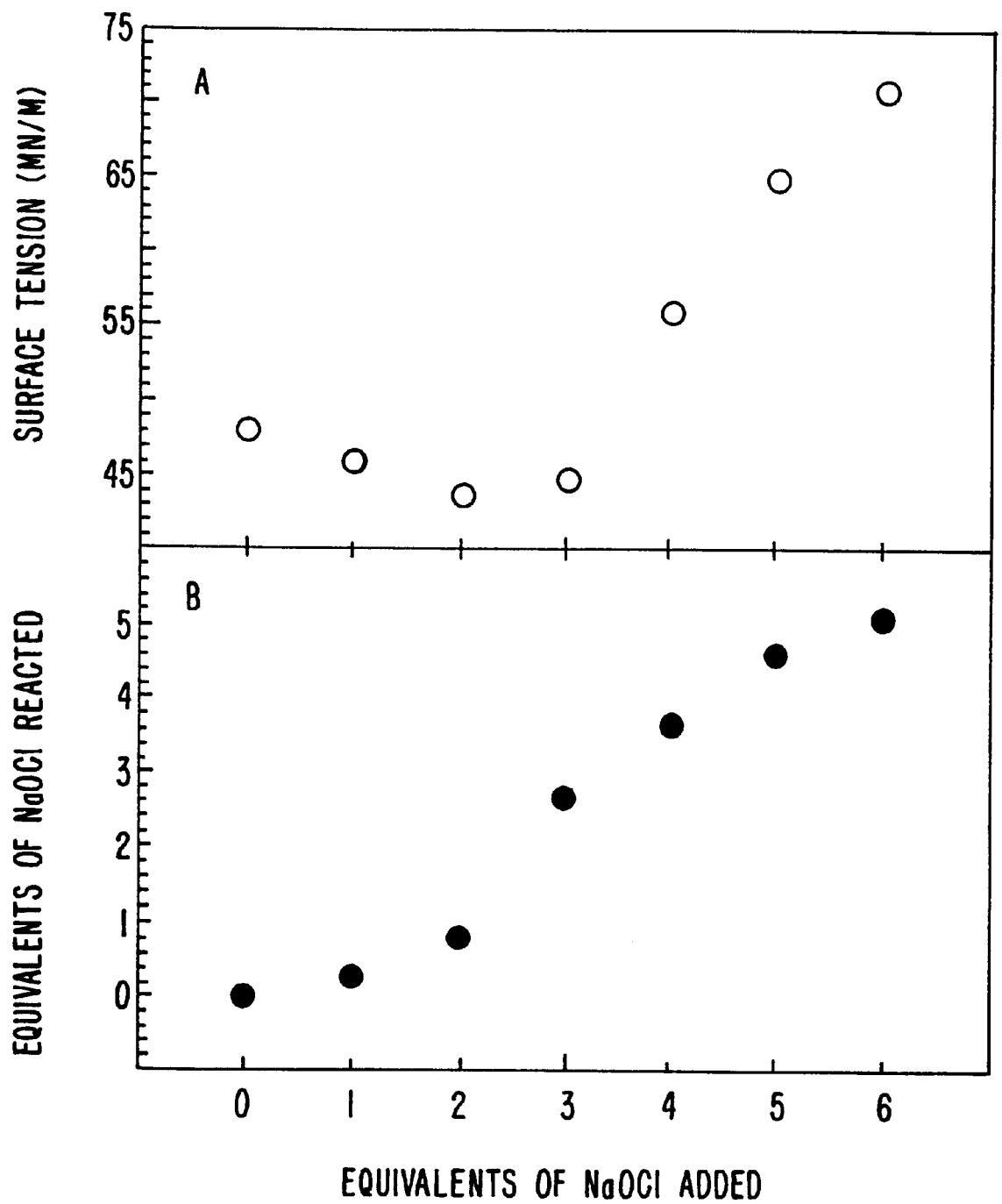
FIG. 15. (A) Surface tensions of a 2 mM aqueous solution of 1 (50 mM phosphate buffer, pH 6.9) after addition of NaOCl (1 to 6 equivalents). The surface tensions were measured using a pendant drop. (B) Equivalents of NaOCl reacted upon the addition of the NaOCl to the solution described in (A).

To test the idea that oxidation of 1 by NaOCl would transform 1 into less surface-active products, changes in surface tensions that accompanied additions of aliquots of NaOCl to solutions of 1 were measured. The amount of $OCl^-$ consumed by reaction with 1 was also determined by iodometry. The initial surface tension of the 2 mM solution (using the pendant drop technique) was measured to be 48 mN/m. Inspection of FIG. 15 reveals that addition of the first two equivalents of NaOCl caused the surface tension to decrease by 4 mN/m to 44 mN/m. The addition of subsequent aliquots of NaOCl, however, caused the surface tension to increase to ~71 mN/m. Whereas 6 equivalents of NaOCl were needed to cause the surface tension to increase from 48 to 71 mN/m, iodometry revealed that only 5.1 equivalents of $OCl^-$ were consumed during the accompanying reaction. That is, a 15% excess of $OCl^-$ remained in solution after the reaction had caused the surface tension to increase to 71 mN/m. We also found that addition of 5 equivalents of NaOCl to a 2 mM solution of 1 could cause a large change in the surface tension (from 48 to 65 mN/m, $\Delta\gamma=17$ mN/m). In this case, only ~8% of the $OCl^-$ added remained unreacted.

Because a past study of the stability of NaOCl in the presence of surfactants such as sodium linear alkanesulfonates, sodium linear alkylbenzenesulfonates, and octylpyrrolidinone indicated that NaOCl decomposed slowly over a period of several days, the stability of NaOCl in aqueous solutions at pH 3, 6.9, and 11 over intervals of time similar to those used in the present experiments was measured (see, Rosen et al., *J. Am. Oil. Chem. Soc.* 69: 667–671 (1992)). That there was no measurable loss of $OCl^-$ over periods of minutes was confirmed by iodometric titration. In view of these results, the $OCl^-$ consumed upon its addition to aqueous solutions of 1 is likely the result of a reaction of $OCl^-$ with 1. Also, the volume of NaOCl necessary to oxidize the aqueous solution of 1 is small (~0.5–2.5% of total volume of solution) and does not significantly affect the concentration of surfactant in solution. In addition, a control experiment was performed in which NaOCl was added to the electrolyte solution (phosphate buffer) and found not to reduce the surface tension of the solution.

Figure 16:
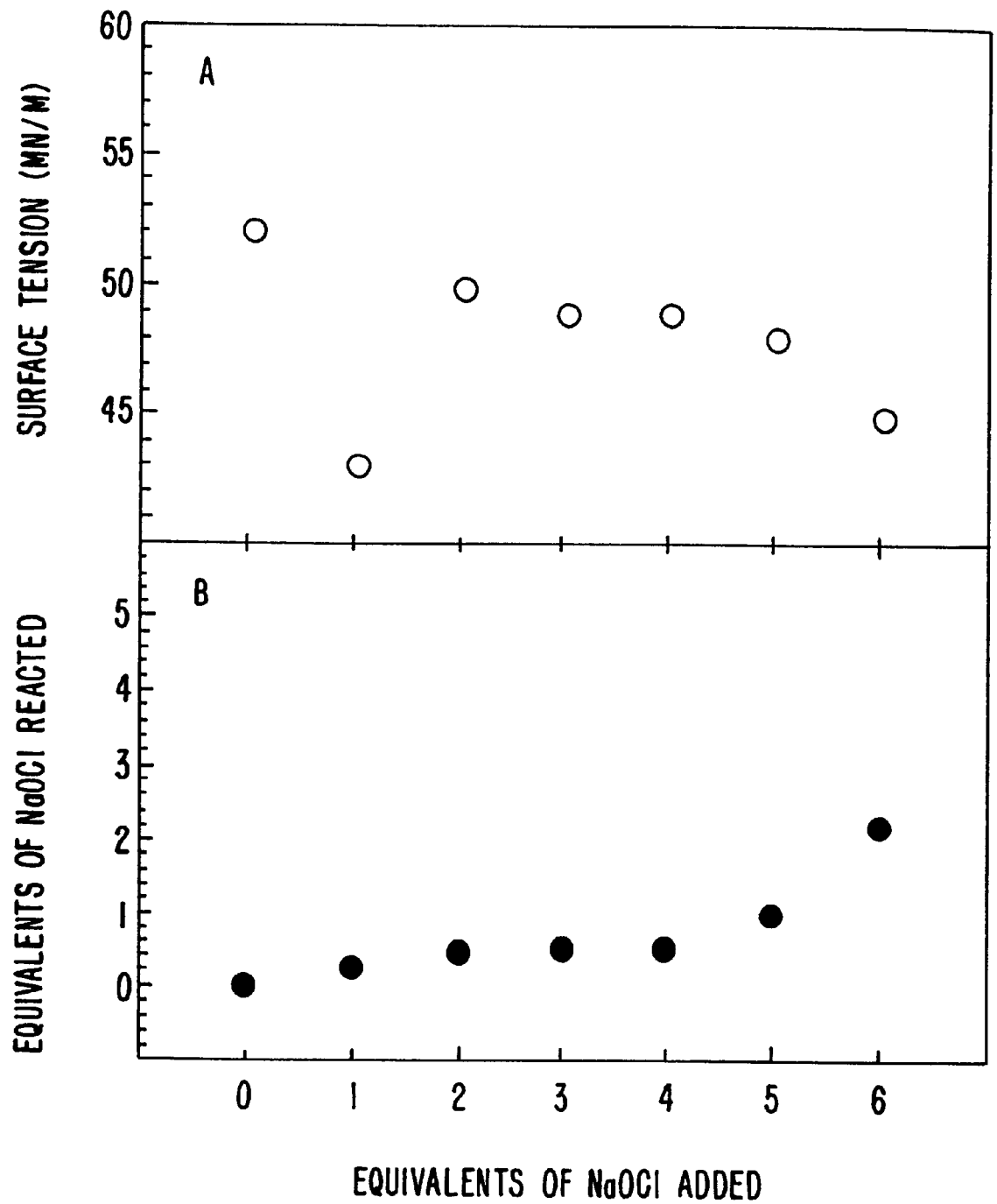
FIG. 16. (A) Surface tensions of a 4 mM aqueous solution (50 mM phosphate buffer, pH 6.9) of DTAB following the addition of NaOCl. The surface tensions were measured using a pendant drop. (B) Equivalents of NaOCl reacted upon the addition of Δ NaOCl to the solution described in (A).

During the addition of NaOCl to a solution of 1, a change in the color of the solution was observed. The addition of the first 3 equivalents of NaOCl to a 2 mM solution of 1 resulted in the initially colorless solution turning yellow. Further additions of NaOCl, however, caused the solution to return to its colorless state. To explore the origin of this color change, an experiment was performed in which 1–6 equivalents of NaOCl (equivalents based on a 2 mM solution of 1) were added to a 4 mM solution of dodecyltrimethylammonium bromide (DTAB). The solution of DTAB was observed to become yellow in color upon addition of the first and second equivalents of NaOCl. However, further additions of NaOCl (between 3–6 equivalents) caused the solution to return to its colorless state. This observation led us to conclude that the yellow color was not due to the interaction of the NaOCl with the disulfide bond of 1, but was instead caused by the presence of either the trimethylammonium head groups of the surfactant or the bromide counterions. That 2.2 equivalents of NaOCl were consumed upon addition of 6 equivalents of NaOCl to a solution of DTAB was measured (FIG. 16). In order to determine whether the reaction of 2.2 equivalents of NaOCl was due to the interaction of NaOCl with the trimethylammonium head groups of the surfactant or the bromide counterions, NaOCl was added to a solution of sodium bromide and the solution was observed to turn yellow. Furthermore, the addition of NaOCl to a 4 mM solution of cetyltrimethylammonium chloride (CTAC) did not cause the solution to become yellow. These results lead to the conclusion that the yellow color observed during the oxidation of 1 by NaOCl was caused by a reaction between NaOCl and the bromide counterions (and can be avoided by using a different counterion).

Also measured was the surface tensions of the aqueous solutions of DTAB upon addition of NaOCl. Addition of the first equivalent of NaOCl to a 4 mM solution of DTAB caused the surface tension to decrease to ~43 mN/m (FIG. 16). The second equivalent of NaOCl caused the surface tension to rise to a value of ~50 mN/m, a value that is lower than the surface tension of the initial solution (~52 mN/m). Subsequent additions (up to six equivalents) of NaOCl resulted in further decreases in surface tension (to 45 mN/m). While the origins of the changes in surface tension reported in FIG. 16 have not been investigated, it is noted that the overall effect of NaOCl on the surface tension of DTAB is opposite to that observed with an aqueous solution of 1.

The results of the above experiments lead to two conclusions. First, although 5.1 equivalents of NaOCl are required to increase the surface tension of the aqueous solution of 1 to 71 mN/m, a portion of these 5.1 equivalents of NaOCl is consumed by a reaction with bromide counterions. Second, because the surface tensions of solutions of DTAB decrease upon addition of NaOCl, the increase in surface tensions of solutions of 1 are attributed to oxidation of the disulfide bonds of 1.

Example 10

This Example illustrates the characterization of the product of the oxidation of 1.

10.1 Materials and Methods

NMR. $^1$H NMR spectra were recorded on a Bruker DMX-400 instrument.

Optical Absorption Spectrophotometry. UV-Vis absorption spectra were measured using a Cary 1E spectrophotometer (Varian) between 190 nm and 300 nm. Measurements were performed using quartz cuvettes.

Electrospray Ionization Mass Spectra. Electrospray ionization mass spectra were recorded at the University of Wisconsin Biotechnology Center using a Perkin Elmer Sciex API 165 spectrometer.

10.2 Results

The oxidation product resulting from the addition of a 6:1 ratio of NaOCl to an aqueous solution of 1 was characterized by using NMR spectroscopy, UV-Vis spectrophotometry, and ESIMS.

NMR. By using $D_2O$ as the reference solvent, the conversion of 1 to 4 was determined to be accompanied by a shift in the peak position of the methylene group adjacent to disulfide from 2.70 ppm to 2.84 ppm. This shift is consistent with the transformation of a disulfide to either a sulfoxide, sulfone, or sulfonate (Silverstein et al., *Spectrometric Identification of Organic Compounds*, 5th Ed., Wiley: New York, 1991).

UV-/Vis. Whereas aqueous solutions of 1 exhibited an absorption peak at ~200±1 nm, aqueous solutions of 4 exhibited an absorption peak at 205±1 nm. The latter peak position is characteristic of sulfoxides or sulfonates (Silverstein et al., supra). Sulfones typically absorb at <180 nm (which was not measurable with our instrument).

ESIMS. The molecular weight of oxidized 1 was determined by ESIMS to be 251.9 g/mole, which is consistent with the formation of a sulfonate product having the following structure $N^+(CH_3)_3$—$(CH_2)_8$—$SO_3^-$. The calculated molecular weight of this proposed structure is 251.4 g/mole. No bromide or chloride counterions were detected by ESIMS.

Figure 11:
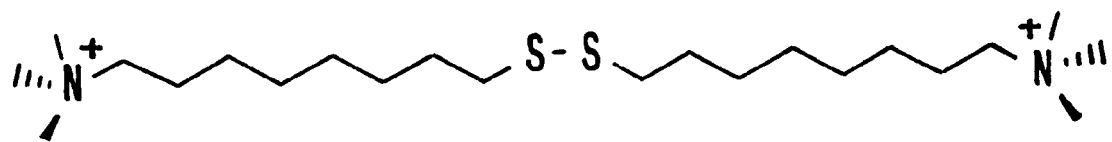
FIG. 11. Structures of bis(8-trimethylammonium bromide)dioctyl disulfide (1), octyl-1-trimethylammonium-8-sulfonate (5), and hexadecane-1,16-bis(trimethylammonium)dibromide (6).
Figure 11:
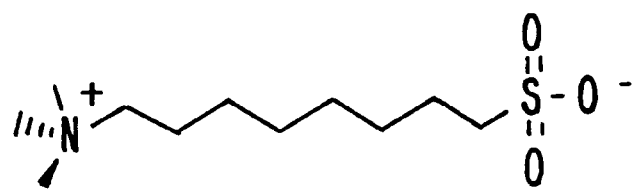
Figure 11:
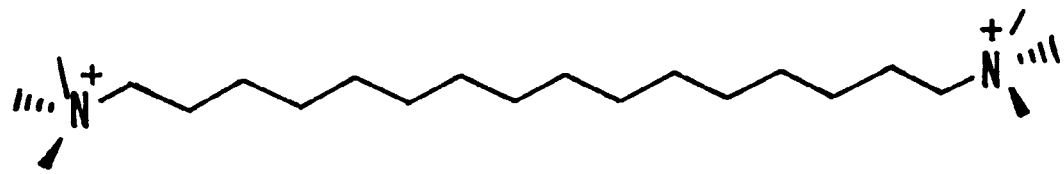
Figure 12:
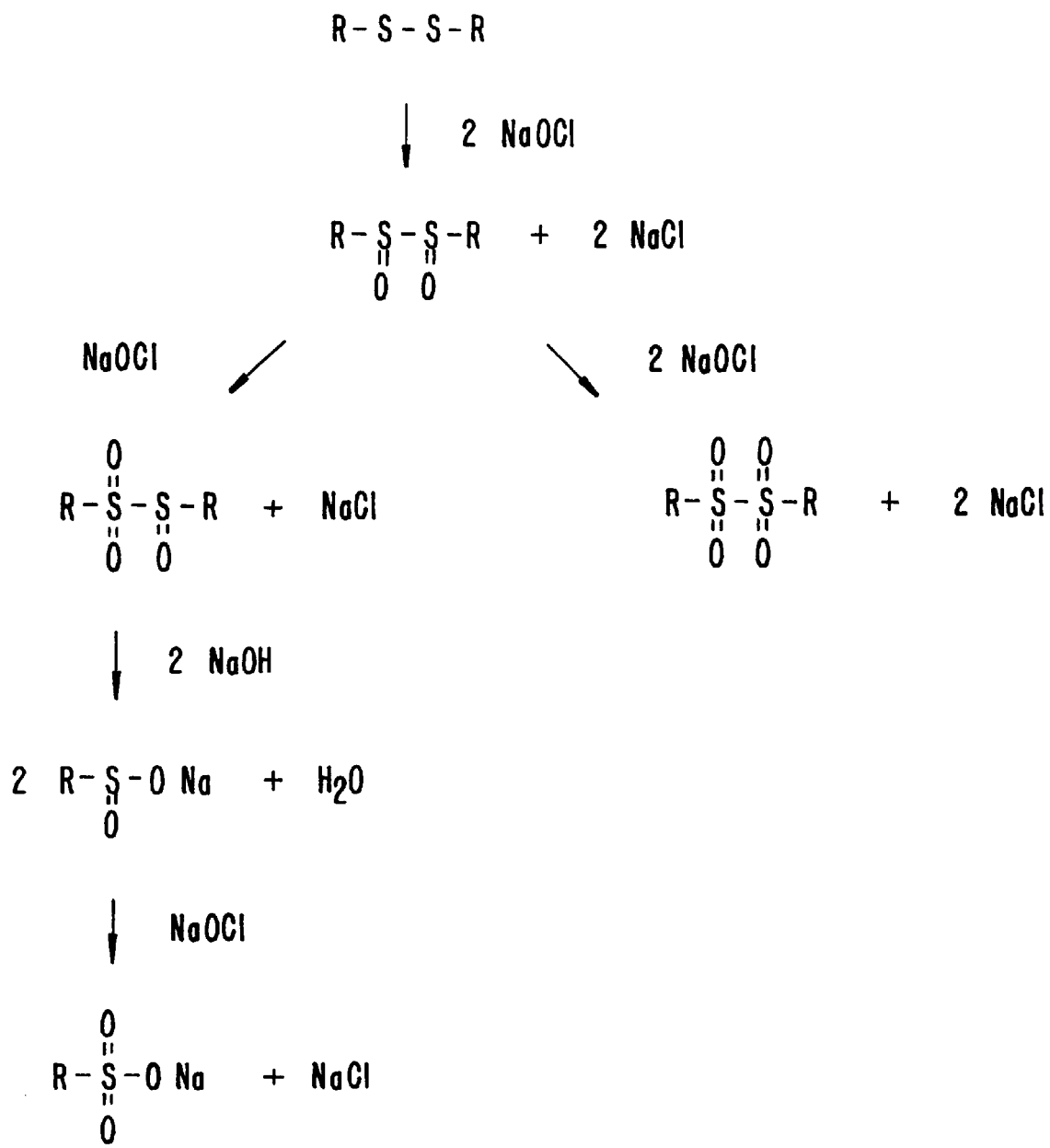
FIG. 12. Proposed reaction path for oxidation of 1 with NaOCl. Adapted from ref 26.

These results, when combined, lead us to the conclusion that 1 is oxidized to a sulfonate species (2) upon the addition of 6 equivalents of NaOCl (see, FIGS. 11 and 12).

Example 11

This Example illustrates the determination of the surface tensions of solutions of compound 4.

A 6:1 ratio of NaOCl to 1 was used to oxidize various concentrations of 1 in aqueous solution. The surface tensions of solutions of 1 following the addition of NaOCl (i.e., solutions of 4) are shown in FIG. 13 (filled circles). The oxidation product (4) remained surface-inactive up to a concentration of 10 mM, whereas the surface tension of the disulfide (surfactant 1) reached its limiting value of 45 mN/m around this concentration. Over the range of concentrations investigated, changes were found in surface tension of up to 24 mN/m to accompany oxidation of 1 to 4 (when using a pendant drop). When using a Wilhelmy plate, changes were measured in equilibrium surface tension of up to 26 mN/m to accompany the oxidation of 1 to 4.

Example 12

This Example illustrates the effect of varying the pH of solutions of compound 1.

Figure 17:
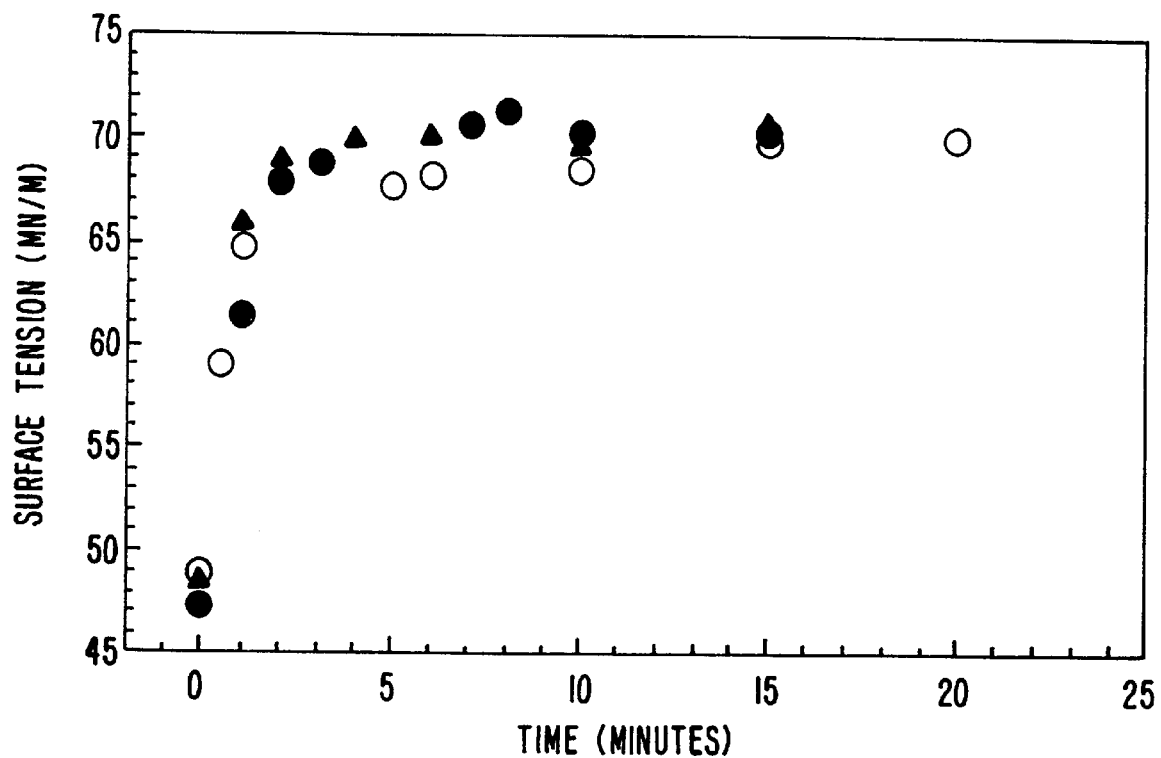
FIG. 17. Surface tensions of 2 mM aqueous solutions of 1 buffered at pH 3 (▲), pH 6.9 (●), or pH 11 (○) following the addition of 6 equivalents of NaOCl. The surface tensions were measured using a pendant drop.

The effect of pH on the oxidation of 1 by NaOCl was investigated, because a chemodegradable surfactant system that is tolerant to variations in pH will prove to be of substantial utility. The oxidation of 1 using NaOCl (6:1 ratio of NaOCl to 1) was performed in 50 mM phosphate buffers at three different pHs (pH 3, 6.9, and 11). Following the addition of NaOCl to aqueous solutions of 1 at pH 3 and pH 6.9, the surface tensions of the solutions were measured to increase from ~48 mN/m to ~71 mN/m within ~5 min (FIG. 17). The surface tension was also determined to increase from ~48 mN/m to ~71 mN/m upon addition of NaOCl to an aqueous solution of 1 at pH 11. In this case, however, it took ~15 min for the surface tension to increase to 71 mN/m. In short, the transformation of 1 to surface-inactive products by addition of NaOCl was tolerant to variations in pH. Therefore disulfide-based surfactants can form the basis of chemodegradable surfactant system that can be used over a wide pH range.

Also measured was the pH accompanying the oxidation of 1 to 2 in water (i.e., in the absence of buffer). Whereas the pH of a 6 mM solution of $OCl^-$ is 10.3, the addition of 6 equivalents of $OCl^-$ to a 1 mM solution of 1 caused the pH of the solution to decrease to 3.3. Three additional equivalents of $OCl^-$ caused the pH of the solution to increase to 8.2.

The conclusions from this experiment are twofold. First, the measurements of the decrease in pH during the oxidation of 1 to 4 are consistent with the reaction pathway in FIG. 12 that leads to formation of the sulfonate product. Second, these results suggest that some level of buffering of the aqueous solutions is necessary so s to maintain the pH of the solution between 6 and 9 upon oxidation of 1 to 4 by NaOCl.

Alternatively, the addition of a small excess of $OCl^-$ can be used to maintain the pH near a neutral value.

Example 13

This Example illustrates that the surfactants of the invention are easily oxidized using commercial bleach.

To demonstrate further the practical utility of this chemodegradable surfactant system, the use of household bleach to oxidize 1 to surface-inactive products was explored. Household bleach was added (6:1 ratio of NaOCl to 1) to a 2 mM solution of 1 in pH 6.9 buffer. Upon addition of bleach to 1, the surface tension of the solution increased from 48 mN/m to ~71 mN/m in ~3 min (FIG. 18A), a result similar to our earlier observations based on the addition of NaOCl to 1. The volume of bleach added was only ~2.5% of the total volume of the solution and, therefore, it did not significantly affect the concentration of the surfactant in solution. A control experiment was performed in which the household bleach was added to the phosphate buffer and found not to change the surface tension. Therefore, that 1 can be readily degraded to surface-inactive products by using commercial formulations of bleach.

Example 14

This Example illustrates the use of the surfactants of the invention to reversibly stabilize an emulsion.

14.1 Materials and Methods 14.1a Formation of Emulsions

A High Intensity Ultrasonic Processor (Fisher, Pittsburgh, Pa.) was used to form an oil-in-water emulsion of 5 wt. % dodecane in 10 mM of 1 (50 mM phosphate buffer, pH 6.9). The mixture was sonicated on a setting of 2 for a period of 20 s and then vortexed for 1 min to ensure that the emulsion was thoroughly mixed.

14.1b Disruption of Emulsions

The disruption of the emulsion was determined by the observation of phase separation in the reaction vial.

14.2 Results

Whether 1 could be used to form emulsions of oil and water that are easily disrupted by the addition of NaOCl was investigated. The adsorption of surfactant at an oil-water interface influences the stability of emulsions droplets through a variety of mechanisms (e.g., by reduction of interfacial tension, by gradients in interfacial tension, or by electrostatic repulsion between oil droplets) (Bibette, et al., *Curr. Opin. Coll. Int. Sci.* 1:746–751 (1996)).

Figure 18:
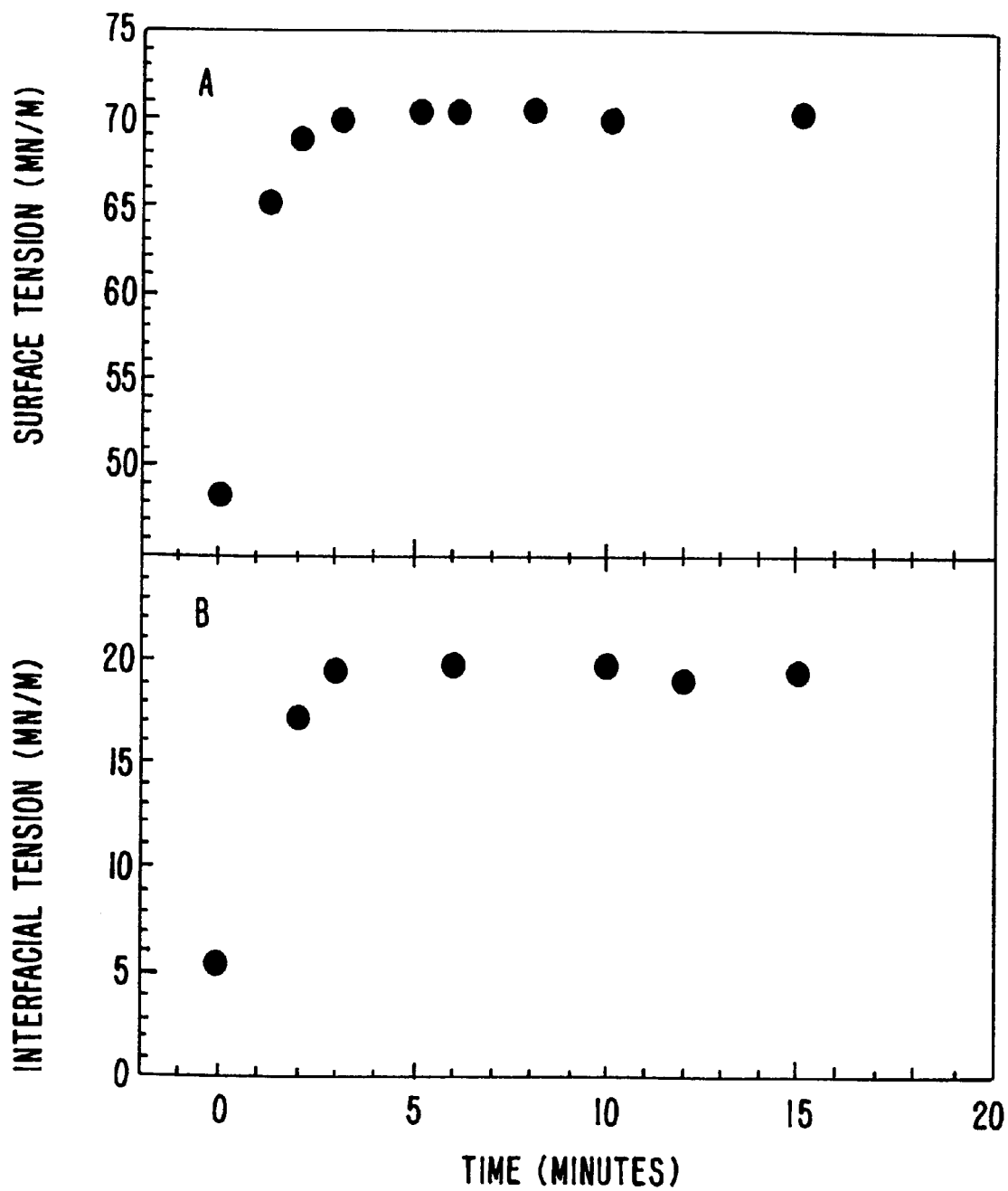
FIG. 18 (A–B). (A) Surface tensions of a 2 mM solution of 1 in 50 mM phosphate buffer, pH 6.9 following the addition of 6 equivalents of NaOCl in a commercial formulation of bleach. (B) Interfacial tensions between dodecane and an aqueous solution (50 mM phosphate buffer, pH 6.9) of 10 mM of 1 following the addition of 6 equivalents of NaOCl to the aqueous solution. The surface and interfacial tensions were measured using a pendant drop.

To determine the extent of adsorption of 1 at an interface between dodecane and an aqueous solution of 1, the interfacial tensions of 10 mM solutions of 1 before, during, and after oxidation by NaOCl were measured (FIG. 18B). Initially, the interfacial tension between dodecane and a 10 mM aqueous solution of 1 was measured to be 6 mN/m. Upon oxidation, the interfacial tension increased to a value of ~20 mN/m within 3 min. This value of the interfacial tension following oxidation of 1 by NaOCl is lower than the interfacial tension reported for dodecane and pure water (~42.5 mN/m). Thus, although a solution of 4 at a concentration of 10 mN was found to be inactive at the surface of water (where the surface pressure is, $\pi=\gamma_o-\gamma=2$ mN/m (FIG. 13)), 4 retains some activity at the interface of dodecane and water ($\pi=22.5$ mN/m). This observation is consistent with past investigations involving sodium dodecyl sulfate (SDS) (Rechfeld, *J. Phys. Chem.* 71:738–745 (1967)). In these studies, the surface pressure of a 1 mM solution of SDS was reported to be 7.5 mN/m at an air-aqueous interface and 15.2 mN/m at the heptadecane-aqueous interface.

Figure 19:
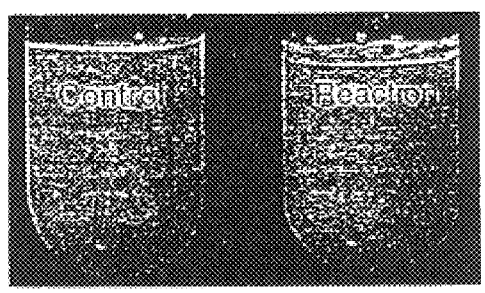
FIG. 19 (A–D). Images of an emulsion formed from 5 wt. % dodecane and 10 mM of 1 in 50 mM phosphate buffer, pH 6.9 (LEFT), and a second identical emulsion following the addition of 6 equivalents of NaOCl (RIGHT). In the absence of NaOCl, the emulsion did not visibly change for at least 24 h. Differences in illumination gave rise to the slight variations in the optical appearance of the control samples. Phase separation was not apparent in the control vial for at least 24 h.
Figure 19:
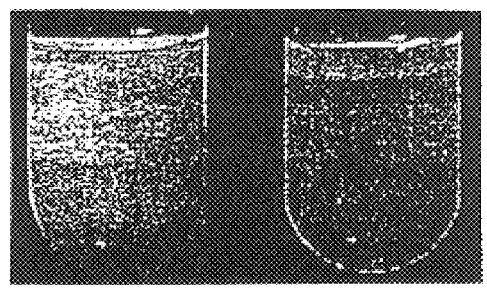
Figure 19:
Figure 19:
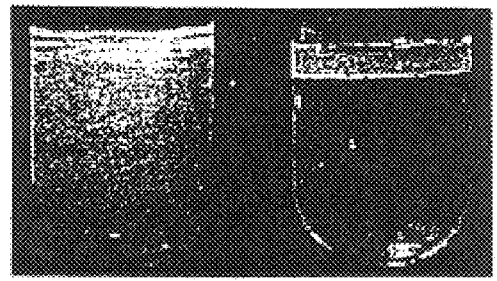
Figure 20D:
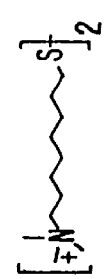
FIG. 20. A Table displaying known cleavable surfactants.

Also explored was the effect of the oxidation of 1 by NaOCl on the stability of .n emulsion formed from a 10 mM solution of 1 and 5 wt. % dodecane. A single emulsion was first divided into two vials. NaOCl (6:1 ratio of NaOCl to 1) was added to one vial so as to initiate the oxidation of 1 (reaction). The second vial was used as a control. Images of the emulsions were captured every 5 min over a 45-min period (FIG. 19). While the vial containing the reaction showed evidence of phase separation within ~10 min (reaching completion after 45 min), the emulsion in the control vial remained intact and did not undergo visible change over 24 hrs. These results demonstrate that 1 and NaOCl can form the basis of a surfactant system that permits the disruption of emulsions upon demand.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A substantially water-soluble surfactant having the formula:

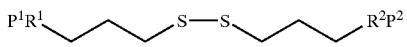

wherein

P¹ and P² are members independently selected from the group consisting of carboxylate, phosphate, sulfate, sulfite, amide, imidazole, protonated amine oxide, phosphonium, hydroxyl, carboxylic acid ester, alkanolamide, saccharide, poly(ethylene oxide), salts of amino sulfuric acid and salts of amino sulfurous acid; and, R¹ and R² are members independently selected from $C_1$ to $C_{24}$ straight-chain alkyl, $C_1$ to $C_{24}$ branched-chain alkyl, and $C_1$ to $C_{24}$ branched-chain substituted alkyl.

2. A substantially water-soluble surfactant having the formula:

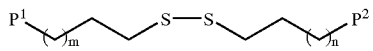

wherein

P¹ and P² are members independently selected from the group consisting of carboxylate, phosphate, sulfate and sulfite, amide, imidazole, protonated amine oxide, phosphonium, hydroxyl, carboxylic acid ester, alkanolamide, saccharide, poly(ethylene oxide), salts of amino sulfuric acid and salts of amino sulfurous acid;

m is a number from 0 to 24, inclusive; and, n is a number from 0 to 24, inclusive.

3. A substantially water-soluble surfactant having the structure:

wherein

P¹ and P² are members independently selected from the group consisting of carboxylate, phosphate, sulfate, sulfite, amide, imidazole, protonated amine oxide, phosphonium, hydroxyl, carboxylic acid ester, alkanolamide, saccharide, poly(ethylene oxide), salts of amino sulfuric acid and salts of amino sulfurous acid;

R¹ and R² are members independently selected from $C_1$ to $C_{24}$ straight-chain alkyl, $C_1$ to $C_{24}$ branched-chain alkyl, $C_1$ to $C_{24}$ and $C_1$ to $C_{24}$ branched-chain substituted alkyl; and, said surfactant remains at least 80% intact after 24 hours in aqueous solution at pH 8 or greater.

4. An aqueous solution comprising a surfactant having the formula:

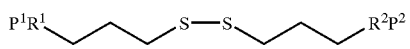

wherein

P¹ and P² are members independently selected from the group consisting of carboxylate, phosphate, sulfate, sulfite, amide, imidazole, protonated amine oxide, phosphonium, hydroxyl, carboxylic acid esters, alkanolamide, saccharide, poly(ethylene oxide), salts of amino sulfurric acid and salts of amino sulfurous acid;

R¹ and R² are members independently selected from $C_1$ to $C_{24}$ straight-chain alkyl, $C_1$ to $C_{24}$ branched-chain alkyl, and $C_1$ to $C_{24}$ branched-chain substituted alkyl; and, said solution is switchable between a first state and a second state by oxidizing the disulfide group of said surfactant.

5. The solution according to claim 4, comprising a mixture of intact surfactant and oxidized surfactant.

6. The solution according to claim 4, wherein said solution is a component of an emulsion and cleaving the disulfide group of said surfactant alters an emulsion characteristic which is a member selected from the group consisting of interfacial tension, interfacial elasticity, interfacial viscosity and combinations thereof.

7. A method for increasing surface tension of an aqueous solution of a surfactant comprising a disulfide moiety, said method comprising:

contacting said solution with an oxidant, thereby oxidizing said disulfide moiety.

8. A method according to claim 7, wherein said surfactant has the structure:

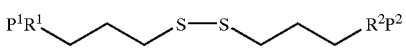

wherein:
P$^1$ and P$^2$ are members independently selected from the group consisting of anionic groups, cationic groups, neutral hydrophilic groups and zwitterionic groups; and
R$^1$ and R are members independently selected from C$_1$ to C$_{24}$ straight-chain alkyl, C$_1$ to C$_{24}$ branched-chain alkyl, C$_1$ to C$_{24}$ straight-chain substituted alkyl and C$_1$ to C$_{24}$ branched-chain substituted alkyl.

9. The method according to claim 8, wherein said surfactant has the structure:

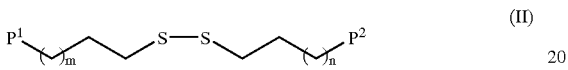

(II)

wherein:
P$^1$ and P$^2$ are members independently selected from the group consisting of anionic groups, cationic groups, neutral hydrophilic groups and zwitterionic groups;
m is a number from 0 to 24, inclusive; and
n is a number from 0 to 24, inclusive.

10. The method according to claim 7, wherein said oxidant is hypochlorite.

11. A method for disrupting an emulsion comprising:
(a) water;
(b) a substantially water-insoluble material; and
(c) a substantially water-soluble surfactant comprising a disulfide moiety,
said method comprising:
contacting said emulsion with an oxidant, thereby oxidizing said disulfide moiety.

12. A method according to claim 11, wherein said surfactant has the structure:

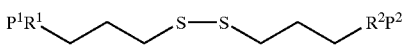

wherein:
P$^1$ and P$^2$ are members independently selected from the group consisting of anionic groups, cationic groups, neutral hydrophilic groups and zwitterionic groups; and
R$^1$ and R$^2$ are members independently selected from C$_1$ to C$_{24}$ straight-chain alkyl, C$_1$ to C$_{24}$ branched-chain alkyl, C$_1$ to C$_{24}$ straight-chain substituted alkyl and C$_1$ to C$_{24}$ branched-chain substituted alkyl.

13. The method according to claim 12, wherein said surfactant has the structure:

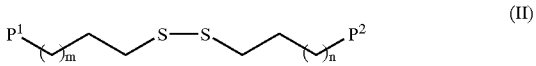

(II)

wherein:
P$^1$ and P$^2$ are members independently selected from the group consisting of anionic groups, cationic groups, neutral hydrophilic groups and zwitterionic groups;
m is a number from 0 to 24, inclusive; and
n is a number from 0 to 24, inclusive.

14. The method according to claim 12, wherein said oxidant is hypochlorite.

15. A method for switching a mixture between an emulsified mixture and a non-emulsified mixture, said emulsified mixture comprising:
(a) water;
(b) a substantially water-insoluble material; and
(c) a substantially water-soluble surfactant comprising a disulfide moiety;
said non-emulsified mixture comprising:
(a) water;
(b) a substantially water-insoluble material; and
(c) a substantially water-soluble surfactant comprising a thiol moiety,
said method comprising;
(a) contacting said emulsified mixture with a reducing agent, thereby cleaving said disulfide and forming said non-emulsified mixture; and
(b) contacting said non-emulsified mixture with an oxidant, thereby producing a disulfide and forming said emulsified mixture.

16. The method according to claim 15, further comprising, repeating steps (a) and (b) more than once.

17. The method according to claim 15, further comprising separating said thiol from said mixture.

18. The method according to claim 17, further comprising, converting said thiol to a disulfide following said separating.

19. A method for producing a transient surface tension reduction in a member selected from an aqueous solution of a substantially water-soluble surfactant comprising a disulfide moiety and an emulsion comprising;
(a) water;
(b) a substantially water-insoluble material; and
(c) a substantially water-soluble surfactant comprising a disulfide moiety,
said method comprising,
contacting said solution or said emulsion with a reducing agent, thereby initiating the reduction of said surfactant and inducing said transient lowering of said surface tension.

20. A method for manipulating surface tension of an aqueous solution of a substantially water-soluble surfactant comprising a disulfide moiety, said method comprising:
applying to said solution a member selected from an oxidizing potential and a reducing potential, thereby altering pH of said aqueous solution and thereby manipulating said surface tension.

21. The method according to claim 20, wherein said solution is a component of an emulsion.

22. The method according to claim 20, wherein said surface tension is varied by from about 1 mN/m to about 15 mN/m.

23. A substantially water-soluble surfactant having the formula:

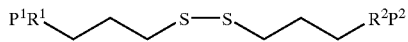

wherein
P$^1$ and P$^2$ are members independently selected from the group consisting of phosphate, sulfate, sulfite, amide, imidazole, protonated amine oxide, phosphonium, hydroxyl, carboxylic acid ester, alkanolamide, saccharide, poly(ethylene oxide), and a zwitterionic group; and, R¹ and R² are members independently selected from $C_1$ to $C_{24}$ straight-chain substituted alkyl radicals.

24. A substantially water-soluble surfactant having the formula:

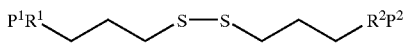

wherein
P¹ and P² are different members selected from the group consisting of an anionic group, a cationic group, a neutral hydrophilic group and a zwitterionic group; and,
R¹ and R² are members independently selected from $C_1$ to $C_{24}$ straight-chain alkyl, $C_1$ to $C_{24}$ branched-chain alkyl, $C_1$ to $C_{24}$ straight-chain substituted alkyl and $C_1$ to $C_{24}$ branched-chain substituted alkyl.

25. A substantially water-soluble surfactant having the structure:

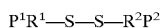

wherein
P¹ and P² are members independently selected from the group consisting of phosphate, sulfate, sulfite, amide, imidazole, protonated amine oxide, phosphonium, hydroxyl, carboxylic acid ester, alkanolamide, saccharide, poly(ethylene oxide), and a zwitterionic group; and,
R¹ and R² are members independently selected from $C_1$ to $C_{24}$ straight-chain substituted alkyl radicals; and,
said surfactant remains at least 80% intact after 24 hours in aqueous solution at pH 8 or greater.

26. An aqueous solution comprising a surfactant having the formula:

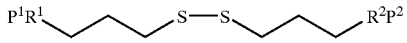

wherein
P¹ and P² are members independently selected from the group consisting of phosphate, sulfate, sulfite, amide, imidazole, protonated amine oxide, phosphonium, hydroxyl, carboxylic acid ester, alkanolamide, saccharide, poly(ethylene oxide), and a zwitterionic group; and,
R¹ and R² are members independently selected from $C_1$ to $C_{24}$ straight-chain substituted alkyl radicals; and,
said solution is switchable between a first state and a second state by oxidizing the disulfide group of said surfactant.

27. A substantially water-soluble surfactant having the formula:

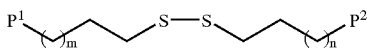

wherein
P¹ and P² are different members selected from the group consisting of an anionic group, a cationic group, a neutral hydrophilic group and a zwitterionic group;
m is a number from 0 to 24, inclusive; and,
n is a number from 0 to 24, inclusive.

28. A substantially water-soluble surfactant having the structure:

wherein
P¹ and P² are different members selected from the group consisting of an anionic group, a cationic group, a neutral hydrophilic group and a zwitterionic group; and,
R¹ and R² are members independently selected from $C_1$ to $C_{24}$ straight-chain alkyl $C_1$ to $C_{24}$ branched-chain alkyl, $C_1$ to $C_{24}$ straight-chain substituted alkyl and $C_1$ to $C_{24}$ branched-chain substituted alkyl; and,
said surfactant remains at least 80% intact after 24 hours in aqueous solution at pH 8 or greater.

29. An aqueous solution comprising a surfactant having the formula:

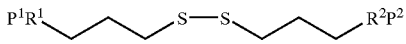

wherein
P¹ and P² are different members selected from the group consisting of an anionic group, a cationic group, a neutral hydrophilic group and a zwitterionic group; and,
R¹ and R² are members independently selected from $C_1$ to $C_{24}$ straight-chain alkyl, $C_1$ to $C_{24}$ branched-chain alkyl, $C_1$ to $C_{24}$ straight-chain substituted alkyl and $C^1$ to $C_{24}$ branched-chain substituted alkyl; and,
said solution is switchable between a first state and a second state by oxidizing the disulfide group of said surfactant.

* * * * *